US009414771B2

(12) United States Patent
McCool

(10) Patent No.: US 9,414,771 B2
(45) Date of Patent: Aug. 16, 2016

(54) NONINVASIVE METHOD AND SYSTEM FOR MEASURING PULMONARY VENTILATION

(71) Applicant: adidas AG, Herzogenaurach (DE)

(72) Inventor: Franklin Dennis McCool, Bristol, RI (US)

(73) Assignee: adidas AG, Herzogenaurach (DE)

( * ) Notice: Subject to any disclaimer, the term of this patent is extended or adjusted under 35 U.S.C. 154(b) by 0 days.

(21) Appl. No.: 14/336,431

(22) Filed: Jul. 21, 2014

(65) Prior Publication Data

US 2014/0323847 A1 Oct. 30, 2014

Related U.S. Application Data

(62) Division of application No. 12/231,692, filed on Sep. 5, 2008, now Pat. No. 8,790,273.

(51) Int. Cl.

*A61B 5/08* (2006.01)
*G01B 7/14* (2006.01)
*G01B 7/30* (2006.01)
*G01R 33/02* (2006.01)
*A61B 5/091* (2006.01)
*A61B 5/113* (2006.01)

(52) U.S. Cl.

CPC ............... *A61B 5/091* (2013.01); *A61B 5/1135* (2013.01)

(58) Field of Classification Search

CPC ........ A61B 5/1135; A61B 5/091; A61B 5/02; G01B 7/14; G01R 33/02
USPC .............. 600/484, 529, 534; 324/217.15, 257
See application file for complete search history.

(56) References Cited

U.S. PATENT DOCUMENTS 5,069,221 A * 12/1991 Smith ................. A61B 5/0535 324/207.2

OTHER PUBLICATIONS

McCool et al, Tidal Volume and Respiratory Timing Derived From a Portable Ventilation Monitor, 2002, Chest, 122:684-691.*

* cited by examiner

*Primary Examiner* — Narayan Bhat
(74) *Attorney, Agent, or Firm* — Sterne, Kessler, Goldstein & Fox P.L.L.C.

(57) ABSTRACT

A pulmonary ventilation system including storage for an empirical relationship that is designed and adapted to determine at least one pulmonary ventilation parameter as a function of a plurality of measured anatomical distances and volume-motion coefficients, acquisition circuitry for acquiring the anatomical distances, a processor for determining the plurality of motion coefficients, and a processor for determining the ventilation parameter based on the acquired anatomical distances and determined plurality of volume-motion coefficients. In one embodiment, the system further includes correlating a base-line ventilation characteristic to the ventilation parameter determined with the empirical relationship.

9 Claims, 19 Drawing Sheets

NONINVASIVE METHOD AND SYSTEM FOR MEASURING PULMONARY VENTILATION

CROSS-REFERENCE TO RELATED APPLICATIONS

This application is a divisional of U.S. application Ser. No. 12/231,692, filed Sep. 5, 2008, now U.S. Pat. No. 8,790,273, which is incorporated herein by reference in its entirety.

FIELD OF THE PRESENT INVENTION

The present invention relates generally to measuring respiratory air volume in humans. More particularly, the invention relates to a noninvasive method for quantitatively measuring pulmonary ventilation and a ventilation system employing same.

BACKGROUND OF THE INVENTION

As is well known in the art, in medical diagnosis and treatment, it is often desirable to quantitatively measure over time the respiratory air volume or pulmonary ventilation. This has conventionally been done by having the patient or subject breathe into a mouthpiece connected to a flow rate measuring device. Flow rate is then integrated to provide air volume change.

There are, however, several drawbacks and disadvantages associated with employing a mouthpiece. A mouthpiece is difficult to use for long term subject monitoring, especially for ill, sleeping or anesthetized subjects. Further, it is uncomfortable for the subject, tends to restrict breathing, and is generally inconvenient for the physician or technician to use.

As is also well known in the art, there are qualitative respiration monitors available that do not require a mouthpiece. Illustrative are the systems disclosed in U.S. Pat. Nos. 3,831,586 and 4,033,332. Although the noted systems eliminate most of the disadvantages associated with a mouthpiece, the systems do not, in general, provide an accurate measurement of air volume. Further, the systems are typically only used to signal an attendant when a subject's breathing activity changes sharply or stops.

Another means for quantitatively measuring respiratory or lung volume is to measure the change in size of the rib cage and abdomen, as it is well known that lung volume is a function of these two parameters. A number of systems and devices have been employed to measure the change in size (i.e. Δ circumference) of the rib cage and abdomen, including mercury in rubber strain gauges, pneumobelts, magnetometers, and respiratory inductive plethysmograph (RIP) belts, see, e.g., D. L. Wade, "*Movements of the Thoracic Cage and Diaphragm in Respiration*", J. Physiol., pp. 124-193 (1954), Mead, et al, "*Pulmonary Ventilation Measured from Body Surface Movements*", Science, pp. 196, 1383-1384 (1967).

In practice, respiratory magnetometers and RIP belts are primarily used to measure the change in size of the rib cage and abdomen. As is well known in the art, respiratory magnetometers consist of tuned pairs of electromagnetic coils or magnetometers; one coil being adapted to transmit a specific high frequency AC electromagnetic field (i.e. transducer) and the other coil (i.e. receiver) being adapted to receive the field. To measure the anteroposterior diameter of the rib cage, a first coil, e.g., transducer, is typically placed over the sternum at the level of the 4th intercostal space and the second coil (of the pair) is placed over the spine at the same level. To measure the anteroposterior diameter of the abdomen, a third coil is typically placed on the abdomen at the level of the umbilicus and a fourth coil (of the pair) is placed over the spine at the same level.

Over the operational range of distances, the output voltage is linearly related to the distance between a pair of coils; provided, the axes of the coils or magnetometers remain parallel to each other. As rotation of the axes can change the voltage, the transducer and receiver coils must be secured to the skin in a parallel fashion and rotation due to the motion of underlying soft tissue that must be minimized.

A potential limitation of the use of such coils or magnetometers is presented in environments that contain large metal structures or electric motors. Such devices produce extraneous electromagnetic fields and consequently affect the magnetometer voltage output.

RIP belts consist of two loops of wire that are coiled and sewed into an elastic belt. To measure changes in cross-sectional areas of the rib cage and abdomen, one belt is secured around the mid-thorax and a second belt is placed around the mid-abdomen.

The voltage change from the belts is generally linearly related to changes in the enclosed cross-sectional area. When the RIP belts are operated in the DC-coupled mode, they can detect shifts in chest wall dimensions, e.g. a change of FRC. However, the AC-coupled mode is typically preferred for tidal volume measurements.

For quantitative measurements, RIP uses a "two-degrees-of-freedom" model to assess changes in perimeters (i.e. cross-sectional area) of the rib cage and abdomen. Since the first rib and adjacent structures of the neck are relatively immobile, the moveable components of the thoracic cavity are taken to be the anterior and lateral walls of the rib cage and the abdomen. Changes in volume of the thoracic cavity will then be reflected by displacements of the rib cage and abdomen.

Displacement (i.e. motion) of the rib cage can be directly assessed. Diaphragm displacement cannot be measured directly, but since the abdominal contents are essentially incompressible, caudal motion of the diaphragm relative to the pelvis and the volume it displaces is reflected by outward movement of the anterolateral abdominal wall.

The "two-degrees-of-freedom" model embraced by most in the field holds that the volume displacement of the respiratory system, i.e. tidal volume ($V_T$), is equal to the sum of the volume displacements of the rib cage and abdomen, i.e.

$$V_T = \alpha RC + \beta Ab \quad \text{Eq. 1}$$

where:

RC and Ab represent linear displacements of the rib cage and abdomen, respectively; and α and β represent volume-motion coefficients.

As is well known in the art, RC and Ab linear displacements are converted to RC and Ab volume displacements when multiplied by the α and β volume-motion coefficients.

It is well established that the use of the noted "two-degrees-of-freedom" model can provide an estimate of $V_T$ that is within 10% accuracy of ventilation measured at the mouth; provided, the subject is confined to one body position.

Two different approaches primarily used for determining the necessary volume-motion coefficients of the rib cage and abdomen are the isovolume technique and the multiple linear regression technique. In the isovolume technique, the subject first performs an isovolume maneuver, shifting volume back and forth between the rib cage and abdominal compartments while holding the glottis closed, whereby there is no net volume change of the system. Since $V_T$ equals zero, Equation 1 can be modified as follows:

$$RC=(-\beta/\alpha)Ab \quad \text{Eq. 2}$$

On a graph of rib cage and abdomen signals, the slope of the isovolume line is equal to the ratio $-\beta/\alpha$.

In practice, the gains of the rib cage and abdomen signals are often adjusted, whereby the slope of the isovolume line equals one. The rib cage and abdomen displacements are thus equal for any volume change. The two signals can then be directly summed to provide volume.

The isovolume method is based on the assumptions that displacements of the surfaces of the rib cage and abdomen are representatively sampled at the measured location, and are similar during isovolume efforts and spontaneous breathing. Since volume-motion coefficients change with posture, the isovolume calibration must be repeated in each body position.

Computer-assisted regression techniques, such as multiple linear regression, are used to determine volume-motion coefficients by solving a matrix of multiple simultaneous equations of changes in chest wall dimensions and lung volume. An advantage of these techniques is that no special calibration maneuver is required to generate volume-motion coefficients.

A limitation of any approach that uses chest wall motion to assess ventilation is, however, that the overall volume change of the chest wall being measured includes not only changes in lung volume, but also blood volume shifts into and out of the thoracoabdominal cavity. This can occur when the respiratory system is subjected to large pressure changes, or with changes in posture (e.g. between supine and upright position).

Another limitation is related to distortion that can occur within the rib cage or abdomen (e.g. between the upper and lower rib cage or between the lower transverse and AP rib cage).

As is well known in the art, the accuracy of "two-degrees-of-freedom" model and, hence, methods employing same to determine volume-motion coefficients of the rib cage and abdomen, is further limited by virtue of changes in spinal flexion that can accompany changes in posture. Indeed, it has been found that $V_T$ can be over or under-estimated by as much as 50% of the vital capacity with spinal flexion and extension, see McCool, et al., "*Estimates of Ventilation From Body Surface Measurements in Unrestrained Subjects*", J. Appl. Physiol., vol. 61, pp. 1114-1119 (1986); and Paek, et al., "*Postural Effects on Measurements of Tidal Volume From Body Surface Displacements*", J. Appl. Physiol., vol. 68, pp. 2482-2487 (1990).

There are two major causes that contribute to the noted "two-degrees-of-freedom" model error(s) and, hence, limitation. A first contributing cause of the error is due to the substantial displacement of the summed rib cage and abdomen signals that occurs with isovolume spinal flexion and extension or pelvic rotation, which is illustrated in FIG. 1.

These shifts are a consequence of conservation of volume. As one of the thoracoabdominal boundaries is pushed in, another must be pushed out.

The second contributing cause of the error is due to posturally-induced changes in volume-motion coefficients. With isovolume spinal flexion, the rib cage comes down with respect to the pelvis and the axial dimension of the anterior abdominal wall becomes smaller. Therefore, less abdominal cavity is bordered by the anterior abdominal wall.

With a smaller anterior abdominal wall surface to displace, a given volume displacement of the abdominal compartment would be accompanied by a greater outward displacement of the anterior abdominal wall. The abdominal volume-motion coefficient would accordingly be reduced.

It has, however, been found that the addition of a measure of the axial motion of the chest wall, i.e. changes in the distance between the xiphoid and the pubic symphysis (Xi), provides a third degree of freedom, which, when employed to determine $V_T$ can reduce the posture related error associated with the "two-degrees-of-freedom" model to within 15% of that measured by spirometry, see Paek, et al., "*Postural Effects on Measurements of Tidal Volume From Body Surface Displacements*", J. Appl. Physiol., vol. 68, pp. 2482-2487 (1990); and Smith, et al. "*Three Degree of Freedom Description of Movement of the Human Chest Wall*", J. Appl. Physiol., Vol. 60, pp. 928-934 (1986).

Smith, et al. proposed the following "three-degrees-of-freedom" model to determine tidal volume, i.e.

$$V_T=\alpha RC+\beta Ab+\gamma Xi \quad \text{Eq. 3}$$

where:

RC and Ab represent linear displacements of the rib cage and abdomen, respectively;

Xi represents the Δ distance between the xiphoid and the pubic symphysis; and

α, β and γ represent volume-motion coefficients for RC, Ab and Xi.

Referring to FIG. 2, there are shown graphical illustrations of % error of estimated $V_T$ determined with one, two and three degrees of freedom models (i.e. x-axis) during various postural movements or maneuvers. It can be seen that the use of a "three-degrees-of-freedom" model incorporating the third independent variable, i.e. the Δ distance between the xiphoid and the pubic symphysis ("Xi"), enhances the accuracy with which volume is estimated from body surface motion in those maneuvers that incorporate changes in spinal attitude.

There are, however, similarly several drawbacks and disadvantages associated with the "three-degrees-of-freedom" model. A major drawback is that the "three-degrees-of-freedom" model reflected in Eq. 3 above is still limited in accuracy to about 15% of actual ventilation in individuals who are doing freely moving postural tasks, such as bending, sitting or standing, due to spinal flexion.

It would thus be desirable to provide an improved method and associated system for determining tidal volume (or pulmonary ventilation) that substantially reduces or eliminates the drawbacks and disadvantages associated with conventional methods and systems that are employed to determine pulmonary ventilation.

It is therefore an object of the present invention to provide noninvasive methods and associated systems for determining pulmonary ventilation that substantially reduce or eliminate the drawbacks and disadvantages associated with conventional methods and systems for determining pulmonary ventilation.

It is another object of the invention to provide noninvasive methods and associated systems for determining pulmonary ventilation that substantially reduce the accuracy errors associated with conventional two-degrees and three-degrees of freedom tidal volume models.

It is another object of the invention to provide noninvasive methods and associated systems for determining pulmonary ventilation that can be readily employed to measure pulmonary ventilation in different postures when awake and during sleep.

It is another object of the invention to provide noninvasive methods and associated systems for determining pulmonary ventilation that can be readily employed to accurately detect respiratory abnormalities.

It is yet another object of the invention to provide noninvasive methods and associated systems for determining pulmonary ventilation that can be readily employed to accurately detect respiratory events, such as apneas and hypopneas, during sleep.

SUMMARY OF THE INVENTION

In accordance with the above objects and those that will be mentioned and will become apparent below, the noninvasive method for measuring pulmonary ventilation, i.e. determining the tidal volume ($V_T$), of a subject, in accordance with one embodiment of the invention, generally comprises the steps of:

(i) determining a first anatomical characteristic representing a first linear displacement of the subject's rib cage in a first orientation, (ii) determining a second anatomical characteristic representing a first linear displacement of the subject's abdomen in the first orientation, (iii) determining a third anatomical characteristic representing a first axial displacement of the subject's chest wall in the first orientation, (iv) determining a first rib cage volume-motion coefficient representing the first orientation of the subject, (v) determining a first abdomen volume-motion coefficient representing the first orientation of the subject, (vi) determining a first chest wall volume-motion coefficient representing the first orientation of the subject, (vii) providing a first mathematical relationship that is adapted to determine $V_T$ of the subject as a function of the first, second and third anatomical characteristics, the first rib cage volume-motion coefficient, first abdomen volume-motion coefficient and first chest wall volume-motion coefficient, and (viii) determining $V_T$ of the subject with the first mathematical relationship and the first, second and third anatomical characteristics, and the first abdomen volume-motion coefficient, first abdomen volume-motion coefficient and first chest wall volume-motion coefficient, whereby the determined $V_T$ represents the subject's $V_T$ at the first orientation.

In one embodiment, the first orientation comprises an upright position.

In one embodiment, the first mathematical relationship comprises the following equation $$V_T=\alpha\Delta RC+(B_u+\epsilon Xi)\Delta Ab+\gamma\Delta Xi$$

wherein $V_T$ represents tidal volume, ARC represents the first anatomical characteristic, ΔAb represents the second anatomical characteristic, ΔXi represents the third anatomical characteristic, $B_u$ represents the value of the abdominal volume-motion coefficient (B) in the upright position, α represents the first rib cage volume-motion coefficient, ($B_u$+ϵXi) represents the abdominal volume-motion coefficient, ϵ represents the linear slope of the relationship of B as a function of Xi, and γ represents the first chest wall volume-motion coefficient.

In one embodiment, the first mathematical relationship comprises the following equation $$V_T=\alpha(\Delta RC)+\beta(\Delta Ab)+\gamma(\Delta Xi)$$

wherein $V_T$ represents tidal volume, ARC represents the first anatomical characteristic, ΔAb represents the second anatomical characteristic, ΔXi represents the third anatomical characteristic, α represents the first rib cage volume-motion coefficient, β represents the first abdominal volume-motion coefficient, and γ represents the first chest wall volume-motion coefficient.

In accordance with another embodiment of the invention, there is provided a method for determining the tidal volume ($V_T$) of a subject, comprising the steps of:

(i) providing a first sensor system adapted to measure linear displacement of the subject's rib cage, said first sensor system including a first transmission coil adapted to transmit at least a first signal and a first receive coil, (ii) providing a second sensor system adapted to measure linear displacement of the subject's abdomen, said second sensor system including a second transmission coil adapted to transmit at least a second signal and a second receive coil adapted to receive said second signal, said first receive coil being adapted to receive said first and second signals, (iii) determining a first linear displacement of the subject's rib cage in a first orientation with said first sensor system, (iv) determining a first linear displacement of the subject's abdomen in said first orientation with said second sensor system;

(v) determining a first axial displacement of the chest wall as a function of said second signal transmitted by said second transmission coil and received by said first receive coil, (vi) determining a first rib cage volume-motion coefficient representing said first orientation of the subject, (vii) determining a first abdomen volume-motion coefficient representing said first orientation of the subject, (viii) determining a first chest wall volume-motion coefficient representing said first orientation of the subject, (ix) providing a first mathematical relationship that is adapted to determine $V_T$ of the subject as a function of said first linear displacement of the subject's rib cage, said first linear displacement of the subject's abdomen, said first axial displacement of the chest wall, said first rib cage volume-motion coefficient, said first abdomen volume-motion coefficient and said first chest wall volume-motion coefficient, and (x) determining $V_T$ of the subject with said first mathematical relationship and said first linear displacement of the subject's rib cage, said first linear displacement of the subject's abdomen, said first axial displacement of the chest wall, said first abdomen volume-motion coefficient, first abdomen volume-motion coefficient and first chest wall volume-motion coefficient, whereby said determined $V_T$ represents the subject's $V_T$ in said first orientation.

In accordance with another embodiment of the invention, there is provided a method for monitoring respiration of a subject, comprising the steps of:

(i) determining a plurality of rib cage volume-motion coefficients representing a plurality of orientations and motions of the subject, (ii) determining a plurality of abdomen volume-motion coefficients representing the plurality of orientations and motions of the subject, (iii) determining a plurality of chest wall volume-motion coefficients representing the plurality of orientations and motions of the subject, (iv) compiling a plurality of volume-motion coefficient data sets, the plurality of volume-motion data sets including a first plurality of volume-motion coefficient data sets representing the plurality of orientations of the subject and a second plurality of volume-motion coefficient data sets representing the plurality of motions of the subject, each of the first plurality of volume-motion coefficient data sets comprising a respective one of the rib cage, abdomen and chest wall volume-motion coefficients that represent a respective one of the plurality of orientations, each of the second plurality of volume-motion coefficient data sets comprising a respective one of the rib cage, abdomen and chest wall volume-motion coefficients that represent a respective one of the plurality of motions, (v) providing a first mathematical relationship that is adapted to determine the tidal volume ($V_T$) of the subject as a function of a first anatomical characteristic representing a first linear displacement of the subject's rib cage, a second anatomical characteristic representing a first linear displacement of the subject's abdomen, a third anatomical characteristic representing a first axial displacement of the subject's chest wall, and a respective one of the plurality of the volume-motion coefficient data sets, (vi) substantially continuously determining the first, second and third anatomical characteristics over a first period of time, (vii) monitoring the orientation of the subject, (viii) determining when the subject is in a selective one of the plurality of orientations, and (ix) substantially continuously determining $V_T$ of the subject over the first period of time with the first mathematical relationship and employing the first, second and third anatomical characteristics determined when the subject is in the respective one of the orientations, and the volume-motion coefficient data set of the first plurality of volume-motion coefficient data sets that represents the selective one of the orientations.

In one embodiment, the method includes the steps of monitoring the motion of the subject, determining when the subject is exhibiting a selective one of the plurality of motions, determining $V_T$ of the subject with the first mathematical relationship and employing the first, second and third anatomical characteristics determined when the subject is in the respective one of the motions, and the volume-motion coefficient data set of the second plurality of volume-motion coefficient data sets that represents the selective one of the motions.

In accordance with another embodiment of the invention, there is provided a pulmonary ventilation system for monitoring respiration of a subject, comprising:

(i) means for substantially continuously determining a first anatomical characteristic representing a first linear displacement of the subject's rib cage in a first orientation, (ii) means for substantially continuously determining a second anatomical characteristic representing a first linear displacement of the subject's abdomen in the first orientation, (iii) means for substantially continuously determining a third anatomical characteristic representing a first axial displacement of the subject's chest wall, (iv) storage means adapted to store a first empirical relationship adapted to determine at least one rib cage volume-motion coefficient, abdomen volume-motion coefficient and chest wall volume-motion coefficient, and a second empirical relationship adapted to determine a ventilation characteristic as a function of the first, second and third anatomical characteristics and the rib cage, abdomen and chest wall volume-motion coefficients, and (v) processing means for determining the ventilation parameter with the second empirical relationship.

In one embodiment of the invention, the system includes means for acquiring at least one base-line ventilation characteristic, and a third empirical relationship adapted to correlate the acquired base-line ventilation characteristic to a ventilation parameter determined with the second empirical relationship.

In one embodiment, the first empirical relationship is adapted to determine a plurality of the rib cage, abdomen and chest wall volume-motion coefficients, the plurality of rib cage, abdomen and chest wall volume-motion coefficients representing a plurality of body orientations and motions.

In one embodiment, the storage means includes a plurality of volume-motion coefficient data sets, the plurality of volume-motion data sets including a first plurality of volume-motion coefficient data sets representing the plurality of orientations and a second plurality of volume-motion coefficient data sets representing the plurality of motions, each of the first plurality of volume-motion coefficient data sets comprising a respective one of the rib cage, abdomen and chest wall volume-motion coefficients that represent a respective one of the plurality of orientations, each of the second plurality of volume-motion coefficient data sets comprising a respective one of the rib cage, abdomen and chest wall volume-motion coefficients that represent a respective one of the plurality of motions.

In one embodiment, the system includes means for detecting when the subject is in one of the plurality of orientations or exhibiting one of the motions.

In one embodiment of the invention, the third empirical relationship is adapted to apply a selective one of the first and second plurality of volume-motion coefficient data sets representing one of the plurality of orientations or motions that corresponds to a detected subject orientation or motion to the first empirical relationship, whereby the processing means determines a first ventilation parameter associated with the detected subject orientation or motion.

In accordance with another embodiment of the invention, there is provided a pulmonary ventilation system for monitoring respiration of a subject, comprising:

(i) a first sensor system adapted to substantially continuously determine a first linear displacement of the subject's rib cage, said first sensor system including a first transmission device adapted to transmit at least a first signal and a first receive device, (ii) a second sensor system adapted to substantially continuously determine a first linear displacement of the subject's abdomen, said second sensor system including a second transmission device adapted to transmit at least a second signal and a second receive device adapted to receive said second signal, said first receive device being adapted to continuously receive said first and second signals, said second signal representing a first axial displacement of the subject's chest wall, (iii) storage means adapted to store a first empirical relationship adapted to determine at least one rib cage volume-motion coefficient, abdomen volume-motion coefficient and chest wall volume-motion coefficient and a second empirical relationship adapted to determine a ventilation characteristic as a function of said first linear displacement of the subject's rib cage, said first linear displacement of the subject's abdomen, said first displacement of the subject's chest wall, and said rib cage, abdomen and chest wall volume-motion coefficients, and (iv) processing means for determining said ventilation parameter with said second empirical relationship.

In one embodiment, each of the first and second receive devices is adapted to receive said first and second signals.

In one embodiment, the first and second receive devices comprise electromagnetic coils.

In one embodiment, the first and second receive devices comprise Hall effect sensors.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE INVENTION

Figure 1:
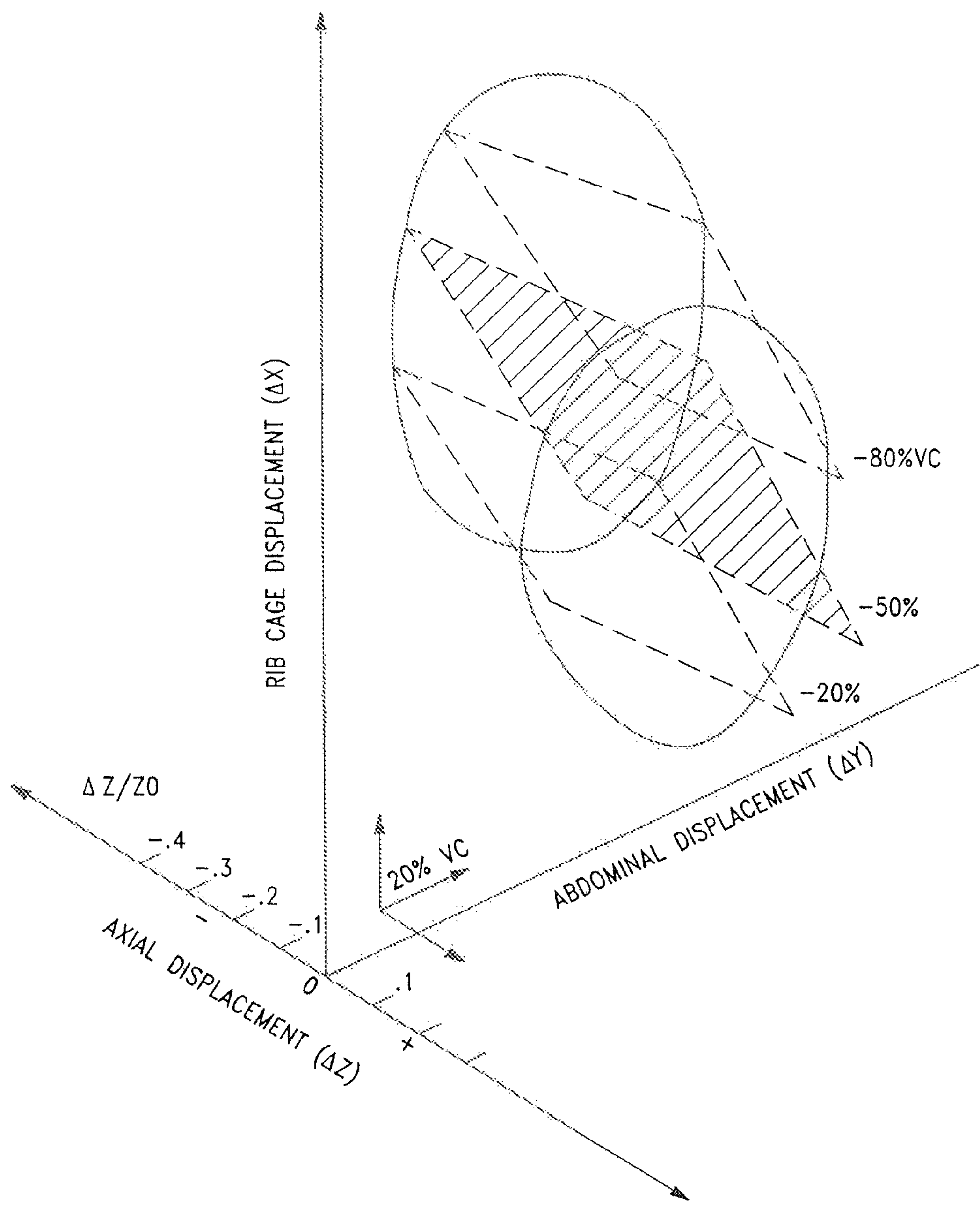
FIG. 1 is a graphic illustration of isovolume lines over a range of spinal flexion and extension or pelvic rotation.
Figure 2:
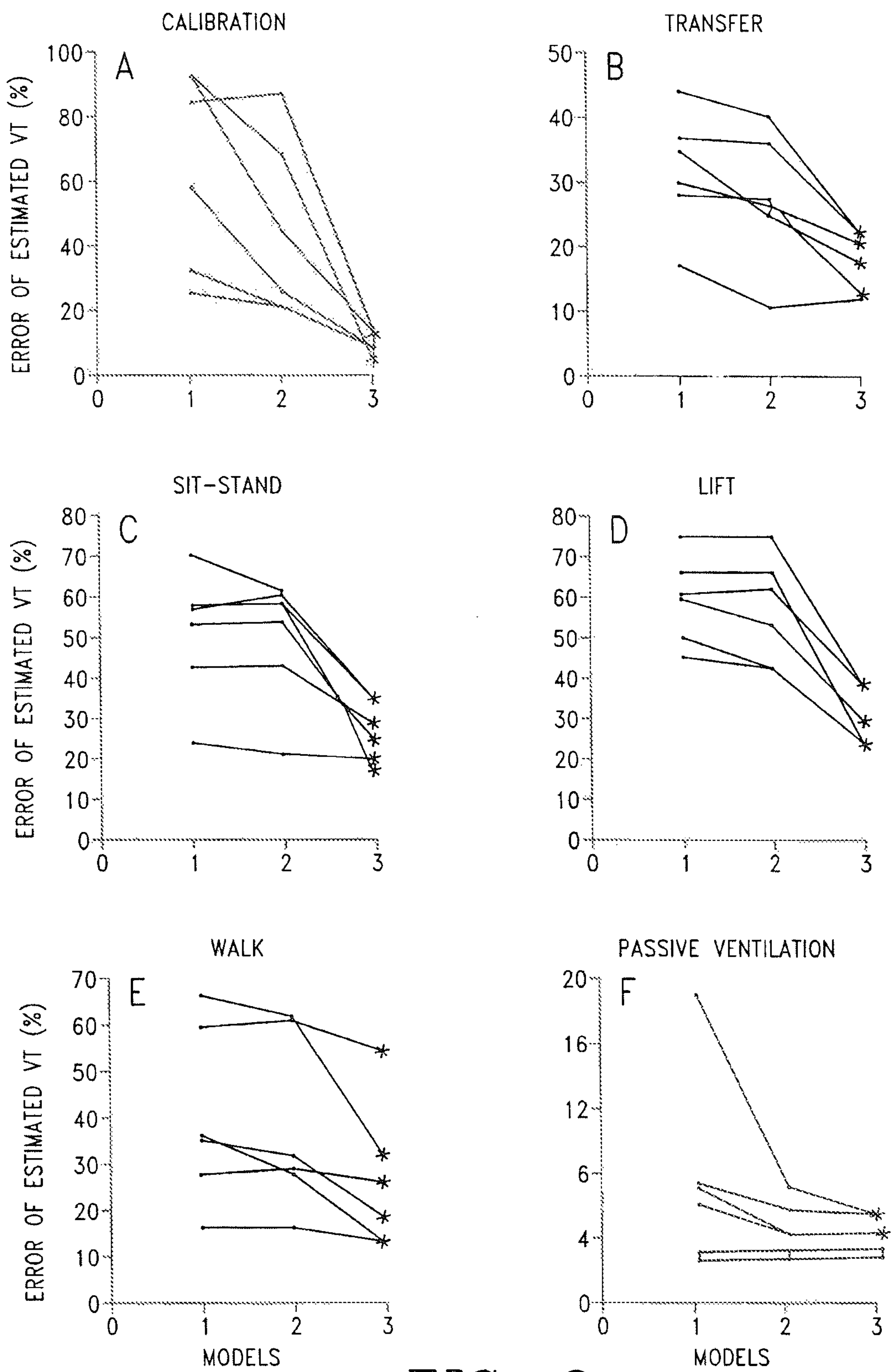
FIG. 2 are comparisons of spirometric volume and volume estimates for five subjects that were estimated using one, two and three degrees of freedom models.

Before describing the present invention in detail, it is to be understood that this invention is not limited to particularly exemplified methods, systems or circuits, as such may, of course, vary. Thus, although a number of methods and systems similar or equivalent to those described herein can be used in the practice of the present invention, the preferred materials and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a, "an" and "the" include plural referents unless the content clearly dictates otherwise. Thus, for example, reference to "an apnea event" includes two or more such events; reference to "a ventilation signal" includes two or more such signals and the like.

DEFINITIONS

The terms "ventilation parameter" and "ventilation characteristic", as used herein, mean and include, a characteristic associated with the respiratory system and functioning thereof, including, without limitation, total pulmonary ventilation, inspiration volume ($V_I$), expiration volume ($V_E$), breathing frequency, inspiratory breathing time and expiratory breathing time.

The term "apnea", as used herein, means and includes the temporary cessation of respiration or a reduction in the respiration rate.

The term "hypopnea", as used herein, means and includes abnormally shallow breathing or a slow respiratory rate.

The terms "respiratory system disorder", "respiratory disorder" and "adverse respiratory event", as used herein, mean and include any dysfunction of the respiratory system that impedes the normal respiration or ventilation process, including, without limitation, an apnea and/or hypopnea.

The terms "patient" and "subject", as used herein, mean and include humans and animals.

As will be appreciated by one having ordinary skill in the art, the present invention is directed to noninvasive methods and associated systems for determining pulmonary ventilation that substantially reduce or eliminate the drawbacks and disadvantages associated with conventional methods and systems for determining pulmonary ventilation. As discussed in detail herein, one major advantage of the present invention is that the noninvasive methods and associated systems for determining pulmonary ventilation substantially reduce the accuracy errors associated with conventional two-degrees and three-degrees of freedom tidal volume models.

A further major advantage of the present invention is that the noninvasive methods and associated systems for determining pulmonary ventilation can be readily employed to monitor breathing in different positions while awake and during sleep, and accurately detect respiratory events, such sleep apnea and hypopnea, during sleep.

As is known in the art, sleep apnea is generally defined as a temporary cessation of respiration during sleep. Obstructive sleep apnea is the recurrent occlusion of the upper airways of the respiratory system during sleep. Central sleep apnea occurs when the brain fails to send the appropriate signals to the breathing muscles to initiate respirations during sleep. Those afflicted with sleep apnea experience sleep fragmentation and complete cessation of respiration (or ventilation) during sleep with potentially severe degrees of oxyhemoglobin desaturation.

Sleep hypopnea is generally defined as abnormally shallow breathing or a slow respiratory rate. Hypopnea differs from apnea in that there remains some air flow.

Monitoring breathing during sleep is the cornerstone to the diagnosis and management of various sleep disorders. The respiratory inductive plythysmograph (RIP) is the most widely used technology in the diagnosis of sleep disorders. As indicated, RIP uses a "two-degrees-of-freedom" model to derive tidal volume ($V_T$) from changes in the circumference (i.e. cross-sectional area) of the rib cage and abdomen.

As is well known in the art, there is a poor correlation between $V_T$ measured by a pneumotachograph and that measured by RIP during sleep. The inaccuracies in the RIP derived $V_T$ have been attributed to slippage of the RIP belts; a factor that would alter RIP calibration, and to changes in posture during sleep. See, e.g., Whyte, et al., "*Accuracy of Respiratory Inductive Plythysmograph in Measuring Tidal Volume During Sleep*", J. Appl. Physiol., vol. 71, pp. 1866-1871 (1991).

As will be appreciated by one having skill in the art, as a subject bends forward, the abdomen contents displace the diaphragm cephalad and this, in turn, expands the rib cage. It has been found that the overestimation of volume due to this "displacement error" can be as great as 40-50% of the vital capacity. See Paek, et al., "*Postural Effects on Measurements of Tidal Volume From Body Surface Displacements*", J. Appl. Physiol., vol. 68, pp. 2482-2487 (1990). Similar inaccuracies with RIP have been noted during sleep in asthmatic subjects with nocturnal bronchospasm and paradoxical chest wall motion. See Ballard, et al., "*Estimates of Ventilation from Inductive Plythysmography in Sleeping Asthmatic Patients*", Chest, vol. 89, pp. 840-845 (1986).

As discussed in detail above, the accuracy of "two-degrees-of-freedom" model is limited by virtue of changes in spinal flexion that can accompany changes in posture. Indeed, it has been found that $V_T$ can be over or under-estimated by as much as 50% of the vital capacity with spinal flexion and extension.

It has, however, been found that the addition of a measure of the axial motion of the chest wall, e.g., Δ distance between the xiphoid and the pubic symphysis (Xi), provides a third degree of freedom, which, when employed to determine $V_T$ can reduce the error associated with the "two-degrees-of-freedom" model.

Although a "three-degrees-of-freedom" model can reduce the error associated with the "two-degrees-of-freedom" model, the "three-degrees-of-freedom" model is still limited in accuracy to about 15% of actual ventilation in individuals who are doing freely moving postural tasks, such as bending, lifting, sitting or standing, due to spinal flexion.

As indicated above, the most pronounced effect of spinal flexion is on the abdominal volume-motion coefficient (β). With bending, β decreases as the xiphi-umbilical distance decreases.

Eq. 3 has accordingly been modified as follows to incorporate the noted dependency:

$$V_T=\alpha(\Delta RC)+(\beta_u+\epsilon Xi)\times(\Delta Ab)+\gamma(\Delta Xi) \quad \text{Eq. 4}$$

where:

ΔRC represents the linear displacement of the rib cage;

ΔAb represents the linear displacement of the abdomen;

ΔXi represents the change in the xiphi-umbilical distance from an upright position;

α represents a rib cage volume-motion coefficient;

β represents an abdominal volume-motion coefficient;

$\beta_u$ represents the value of the abdominal volume-motion coefficient (β) in the upright position;

ϵ represents the linear slope of the relationship of β as a function of the xiphi-umbilical distance Xi;

($B_u$+ϵXi) represents the corrected abdominal volume-motion coefficient; and

γ represents a xiphi-umbilical volume-motion coefficient.

Equation 4 represents a "three-degrees-of-freedom" model, which now reflects the dependence of β on the xiphi-umbilical distance.

According to the invention, tidal volume ($V_T$) can also be determined as a function of changes in the anteroposterior dimensions of the rib cage and abdomen, as well as the axial displacement of the chest wall, i.e.

$$V_T=\alpha(\Delta RC)+\beta(\Delta Ab)+\gamma(\Delta Xi) \quad \text{Eq. 5}$$

where:

ΔRC represents the linear displacement of the rib cage;

ΔAb represents the linear displacement of the abdomen;

ΔXi represents axial displacement of the chest wall;

α represents a rib cage volume-motion coefficient;

β represents an abdominal volume-motion coefficient; and

γ represents a chest wall volume-motion coefficient.

According to the invention, the axial displacement of the chest wall can be determined from various reference points. This is facilitated by the unique multi-functionality of selective coils of the invention and placement thereof (discuss in detail below).

Thus, in one embodiment of the invention, the xiphi-umbilical distance is measured to determine ΔXi. γ would thus represent a xiphi-umbilical volume motion coefficient.

In a preferred embodiment of the invention, the sternal-umbilical distance is measured to determine ΔXi. γ would thus represent a sternal-umbilical volume motion coefficient.

In one embodiment of the invention, the values of volume-motion coefficients α, β and γ are determined for three positions or orientations, i.e. supine, right and left lateral decubitus positions, by multiple linear regressions, as set forth in Stagg, et al., "*Computer-aided Measurement of Breath Volume and Time Components Using Magnetometers*", J. Appl. Physiol., vol. 44, pp. 623-633 (1978); which is expressly incorporated by reference herein. $V_T$ is then calculated after applying the noted volume-motion coefficients to the signals obtained in the same body position.

In one embodiment of the invention, the values of coefficients α, β and γ are determined during a plurality of motions or activities by multiple linear regressions.

The term "volume-motion coefficient", as used herein, thus means both coefficients representing body positions or orientations and motions of a subject.

As will readily be appreciated by one having ordinary skill in the art, the "three-degrees-of-freedom" models of the invention substantially reduce $V_T$ measurement errors associated with conventional two-degrees and three-degrees of freedom models resulting from changes in posture. Indeed, as set forth below, $V_T$, inspiration volume ($V_I$) and expiration volume ($V_E$) can be accurately measured in various postures while awake and during sleep using the "three-degrees-of-freedom" models of the invention.

As discussed in detail below, the "three-degrees-of-freedom" models of the invention can also be readily employed to detect adverse respiration or ventilation events, such as apneas or hypopneas.

Several embodiments of pulmonary ventilation systems of the invention will now be described in detail. It is, however, understood that the invention is not limited to the system embodiments described herein. Indeed, as will be appreciated by one having ordinary skill in the art, systems and associated circuits similar or equivalent to the described systems can also be employed within the scope of the present invention.

In general, the ventilation systems of the invention include means for storing an empirical relationship that is designed and adapted to determine at least one ventilation parameter as a function of a plurality of anatomical measurements and volume-motion coefficients, means for acquiring the anatomical measurements, means for determining the plurality of motion coefficients, and processing means for determining the ventilation parameter based on the acquired anatomical measurements and determined plurality of volume-motion coefficients. In a preferred embodiment, the ventilation system further includes means for acquiring base-line ventilation characteristics and means for correlating the base-line ventilation characteristics to the ventilation parameter determined with the empirical relationship.

The ventilation systems of the invention are also preferably implemented in a compact, light-weight configuration that can be easily attached to or carried by, e.g. carrier vest, an individual being monitored.

Figure 3:
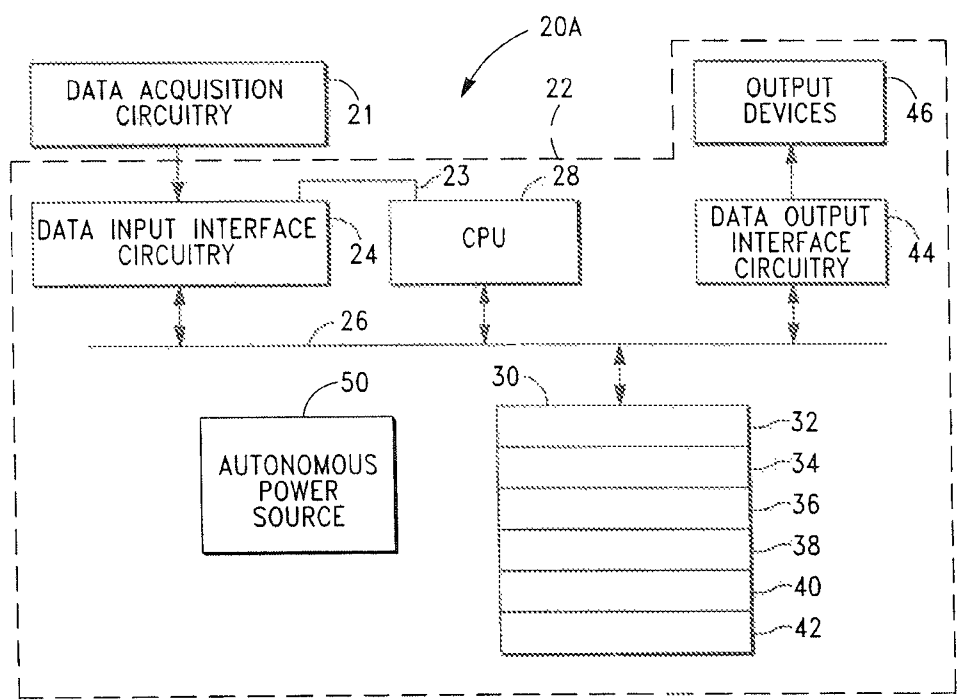
FIG. 3 is a schematic illustration of one embodiment of a pulmonary ventilation system of the invention.

Referring now to FIG. 3, there is shown one embodiment of a pulmonary ventilation system 20A of the invention. As illustrated in FIG. 3, the system 20A preferably includes data acquisition circuitry 21 and data processing circuitry 22.

The system 20A also includes a power source 50, such as a battery. In one embodiment of the invention, the system 20A is operable on 100 mA current from a +/−8.0V to +/−12.0V power source 50.

Figure 4:
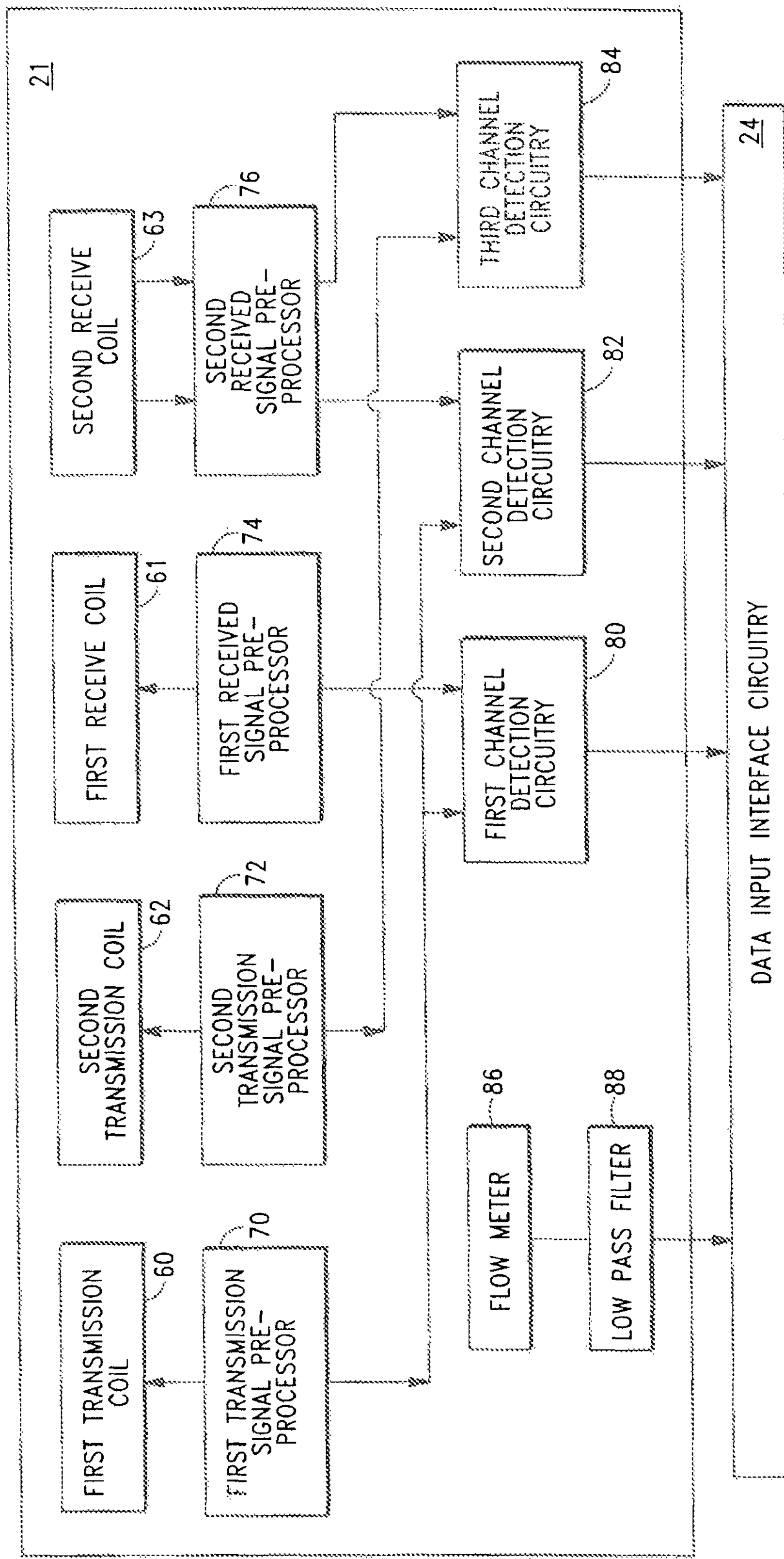
FIG. 4 is a schematic illustration of one embodiment of the pulmonary ventilation system data acquisition circuitry, according to the invention.

According to the invention, the data acquisition circuitry 21 includes data acquisition means, i.e. means for measuring (or sensing) changes in the anteroposterior diameters of the rib cage and abdomen, and axial displacement of the chest wall. In one embodiment of the invention, which is illustrated in FIG. 4 and discussed in detail below, the data acquisition means comprises paired electromagnetic coils 60-63.

It is, however, understood that the invention is not limited to the use of electromagnetic coils to measure changes in the anteroposterior diameters of the rib cage and abdomen, and axial displacement of the chest wall. Indeed, various additional means and devices that can be readily adapted to measure the noted anatomical parameters can be employed within the scope of the invention. Such means and devices include, without limitation, Hall effect sensors and electronic compass sensors.

Referring back to FIG. 3, in the illustrated embodiment, the data processing circuitry 22 includes data input interface circuitry 24, which is adapted to receive data from the data acquisition circuitry 21. According to the invention, the data input interface circuitry 24 facilitates data communication by and between the data acquisition circuitry 21 and the data processing circuitry 22.

In the illustrated embodiment, the data input circuitry 24 is in communication with (i.e. operatively connected to) system buses 23, 26, and transmits (or directs) signals thereto. The central processing unit (CPU) 28 is also preferably operatively connected to buses 23, 26.

As further illustrated in FIG. 3, bus 26 is in communication with memory means (or medium) 30, which includes at least one, more preferably, a plurality of executable programs. In one embodiment of the invention, the programs include a calibration program (or routine) 32, a signal processing or element analysis program 36, a ventilation parameter program 38, and an output program 40.

According to the invention, the central processing unit 28 executes selective programs stored in the memory means 30. The data provided by the programs, e.g. accumulated pulmonary ventilation data 42, and derived volume-motion coefficients are also preferably stored in the memory means 40.

In some embodiments of the invention, the calibration program 32 comprises a routine for determining volume-motion coefficients in selective body positions and/or motions and calibrating the data acquisition circuitry 21. In a preferred embodiment, calibration of the data acquisition circuitry 21 is performed in a single step.

In some embodiments of the invention, the calibration program 32 is also adapted to "automatically" select derived volume-motion coefficients, i.e. a volume-motion coefficient data set, reflecting a specific body position (or posture) or activity to calibrate the data acquisition circuitry 21 when a subject or patient is in the noted body position or performing the activity.

The element analysis program 36 is designed and adapted to perform element analyses on acquired signals (representing acquired data) to reduce any extraneous noise in the signals. In one embodiment of the invention, the element analyses include at least one Fourier analysis. The Fourier analysis, when combined with band pass filtering in the software, facilitates use of the system 20A in ambulatory activities.

In a preferred embodiment, the ventilation parameter program 38 employs at least one of the "three-degrees-of-freedom" models of the invention to determine at least one ventilation parameter, e.g., total pulmonary ventilation.

The output program 40 is designed and adapted to facilitate the visual display of acquired data, which can be displayed on an output device 46, e.g. a liquid crystal display, or, as discussed below, an external output device. As illustrated in FIG. 3, in the noted embodiment, the output device 46 is in communication and, hence, interacts with the CPU 28 through data output interface circuitry 44.

According to the invention, the data output interface circuitry 44 can be adapted to interact with external output devices, such as a personal computer, a printer, a monitor and the like. Communication by and between the data output interface circuitry 44 and external device(s) can be achieved via wired connections therebetween and/or wireless transmission.

As illustrated in FIG. 3, the memory means 30 preferably includes at least one, preferably, a plurality of digital band pass filters 34. According to the invention, the digital band pass filters 34 are designed and employed to eliminate extraneous noise or artifacts resulting from soft tissue motion.

Referring now to FIG. 4, there is shown one embodiment of the data acquisition circuitry 21 of the invention. As illustrated in FIG. 4, the data acquisition circuitry 21 preferably includes a first transmission coil 60, a second transmission coil 62, a first receive coil 61 and a second receive coil 63.

In a preferred embodiment of the invention, at least one of the two receive coils 61, 63 is adapted to receive transmissions (or process signals) from each of the transmission coils 60, 62, i.e. dual functionality.

Accordingly, in one embodiment of the invention, the first transmission coil 60 comprises a first frequency (e.g., 8.97 kHz) transmitter coil, the second transmission coil 62 comprises a second frequency (e.g., 7 kHz) transmitter coil, the first receive coil 61 comprises a first frequency receive coil, and the second receive coil 63 comprises a first/second frequency (7/8.97 kHz based on the noted first and second frequency examples) receive coil.

As will be appreciated by one having ordinary skill in the art, the dual functionality of the second receive coil 63 reduces the number of receive coils, thereby reducing the number of attachments to a patient simplifying system design, and reducing power requirements.

In some embodiments of the invention, each receive coil 61, 63 is adapted to receive transmissions from each of the transmission coils 60, 62. As discussed in detail below, the dual functionality of both receive coils 61, 63 enhances the accuracy of anatomical measurements determined from transmissions by and between the coils 60-63.

Figure 5A:
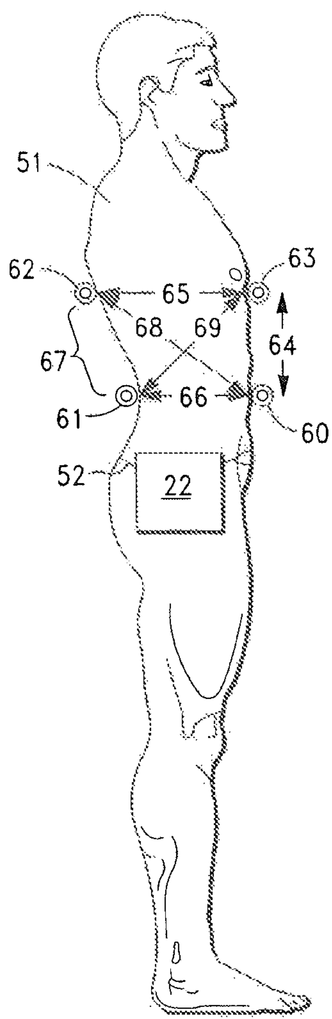
FIG. 5A is a side view of a subject, showing the positioning of the data acquisition circuitry shown in FIG. 4, according to one embodiment of the invention.

Referring now to FIG. 5A, there is shown the positioning of the coils 60-63 and data processing circuitry 22 on a subject or patient 51, in accordance with one embodiment of the invention. As illustrated in FIG. 5A, the first transmission coil 60 is positioned on the front of the subject 51 proximate the umbilicus of the subject 51 and the first receive coil 61 is preferably positioned at the same axial position, but on the back of the subject 51. The second receive coil 63 is positioned on the front of the subject 51 proximate the base of the sternum of the subject 51 and the second transmission coil 62 is located at the same axial position, but on the back of the subject 51.

In the illustrated embodiment, the data processing circuitry 22 is attached to the subject 51 via a belt 52.

According to the invention, the positions of the transmission coils 60, 62 and receive coils 61, 63 can be reversed, i.e. transmission coil 60 and receive coil 63 placed on the back of the subject 51 and transmission coil 62 and receive coil 61 placed on the front of the subject.

As discussed in detail below, both transmission coils 60, 62 can also be placed on the front or back of the subject and the receive coils 61, 63 can be placed on the opposite side.

As stated, in one embodiment of the invention, the second receive coil 63 is adapted to receive and process signals from both the first and second transmission coils 60, 62, reducing the number of coils required to determine $V_T$ (using a "three-degrees-of-freedom" model of the invention) from six to four. This simplifies the instrumentation attached to a subject, and reduces the power requirements of the system 20A.

According to the invention, the coils 60-63 can be attached to the subject by various suitable means. In one embodiment of the invention, the coils 60-63 are attached to the subject 51 via medical tape.

Referring back to FIG. 5A, arrow 64 represents the Xi or, in this instance, the xiphi-umbilical distance. Arrow 65 represents the rib cage-anteroposterior (RC-AP) distance, while arrow 66 represents the abdomen-anteroposterior (Ab-AP) distance.

FIG. 5 thus illustrates the three degrees of freedom or motion (RC-AP, Ab-AP, and Xi) that are measured in accordance with the invention. According to the invention, as the subject or patient breathes, the change in distance between each pair of coils 60, 61 and 62, 63 (denoted by arrows "65" and "66") is sensed. The change in distance between the paired coils corresponds to changes in voltage that is a function of changes in the anteroposterior distance of the rib cage (RC-AP) and the abdomen (Ab-AP).

The axial displacement of the chest wall (denoted by arrow "64"), e.g., xiphi-umbilical distance (Xi), is also measured. In one embodiment of the invention, wherein coil 63 comprises a dual functionality coil, the axial displacement of the chest wall is directly determined from sensed changes in voltage between transmission coil 60 and receive coil 63.

In one embodiment of the invention, wherein receive coils 61 and 63 comprise dual functionality coils, the axial displacement of the chest wall is similarly determined from sensed changes in voltage between transmission coil 60 and receive coil 63. However, in this instance, the sensed changes in voltage between transmission coil 62 and receive coil 61, reflecting the distance between the points of attachment of coils 62 and 61 (denoted length "67") can be correlated with the sensed changes in voltage between transmission coil 60 and receive coil 63.

In one embodiment of the invention, receive coils 61 and 63 similarly comprise dual functionality coils. However, in this embodiment, both receive coils 61, 63 are placed on the same side of the subject's body and the transmission coils 60, 62 are placed on the opposite side of the subject's body.

Figure 5B:
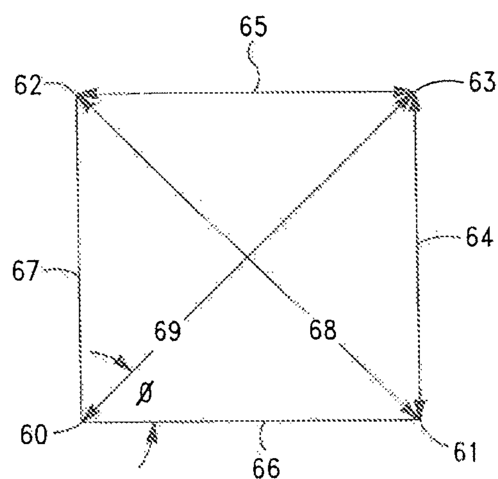
FIG. 5B is a schematic illustration of the geometric configurations defined by the points of attachment of transmission and receive coils, according to one embodiment of the invention.

By virtue of the placement of coils 60-63 and the dual functionality of receive coils 61, 63, various known empirical (e.g., trigonometric) relationships can be employed to determine the axial displacement of the chest wall based on the geometrical configurations defined by the points of attachment of the coils 60-63, and measured lengths therebetween (see FIG. 5B). By way of example, if the triangle defined by coils 60, 61 and 63, i.e. attachment points thereof, is deemed a right triangle, and the distances of lengths "66" and "69" equal x and y, respectively, the change in distance of length "64", i.e. chest wall displacement (ΔXi) can be determined as follows:

$$\Delta Xi = Xi - ((L_{69})^2) - (L_{66})^2)) \qquad \text{Eq. 6}$$

where:

Xi represents the original axial chest wall distance, as measured between two selective positions, e.g., xiphi-umbilical distance;

$L_{69}$ represents the length denoted "69"; and $L_{66}$ represents the length denoted "66".

If $L_{69}$ and $L_{66}$, and angle ϕ are known, the law of cosines can be employed to determine the length "64" and changes thereof, i.e. chest wall displacement (ΔXi).

As will also be readily appreciated by one having ordinary skill in the art, the use of two dual functionality receiver coils, e.g., receive coils 61, 63, and the placement thereof on one side of the subject facilitates simple and accurate determination of axial displacement of the chest wall, regardless of the axial placement of the receive coils 61, 63 (provided, the receive coils 61, 63 remain substantially axially aligned).

The use of two dual functionality receiver coils, e.g., receive coils 61, 63, and the placement thereof on one side of the subject also facilitates accurate determination of whether a measured displacement of the rib cage actually reflects true ventilation of a subject.

According to the invention (and discussed in detail below), the acquired data representing the noted measured distances is employed by the ventilation parameter program 38 of the invention to determine one or more ventilation parameters or characteristics.

Referring back to FIG. 4, in the illustrated embodiment, a first transmission signal pre-processor 70 transmits a signal to the first transmission coil 60. Similarly, a second transmission signal processor 72 transmits a signal to the second transmission coil 62.

The received signals are then processed by three channels, including a first detection circuitry channel 80, a second detection circuitry channel 82, and a third detection circuitry channel 84. The output of the individual channels is preferably transmitted to the data input interface circuitry 24 for subsequent processing and storage by the CPU 28, in accordance with the executable programs stored in memory 30.

The data acquisition circuitry 21 also includes a flow meter 86, whose output is preferably processed by a low pass filter 88 before being transmitted to the data input interface circuitry 24. The data provided by the flow meter 86 is employed during the calibration step, as discussed below.

Figure 6:
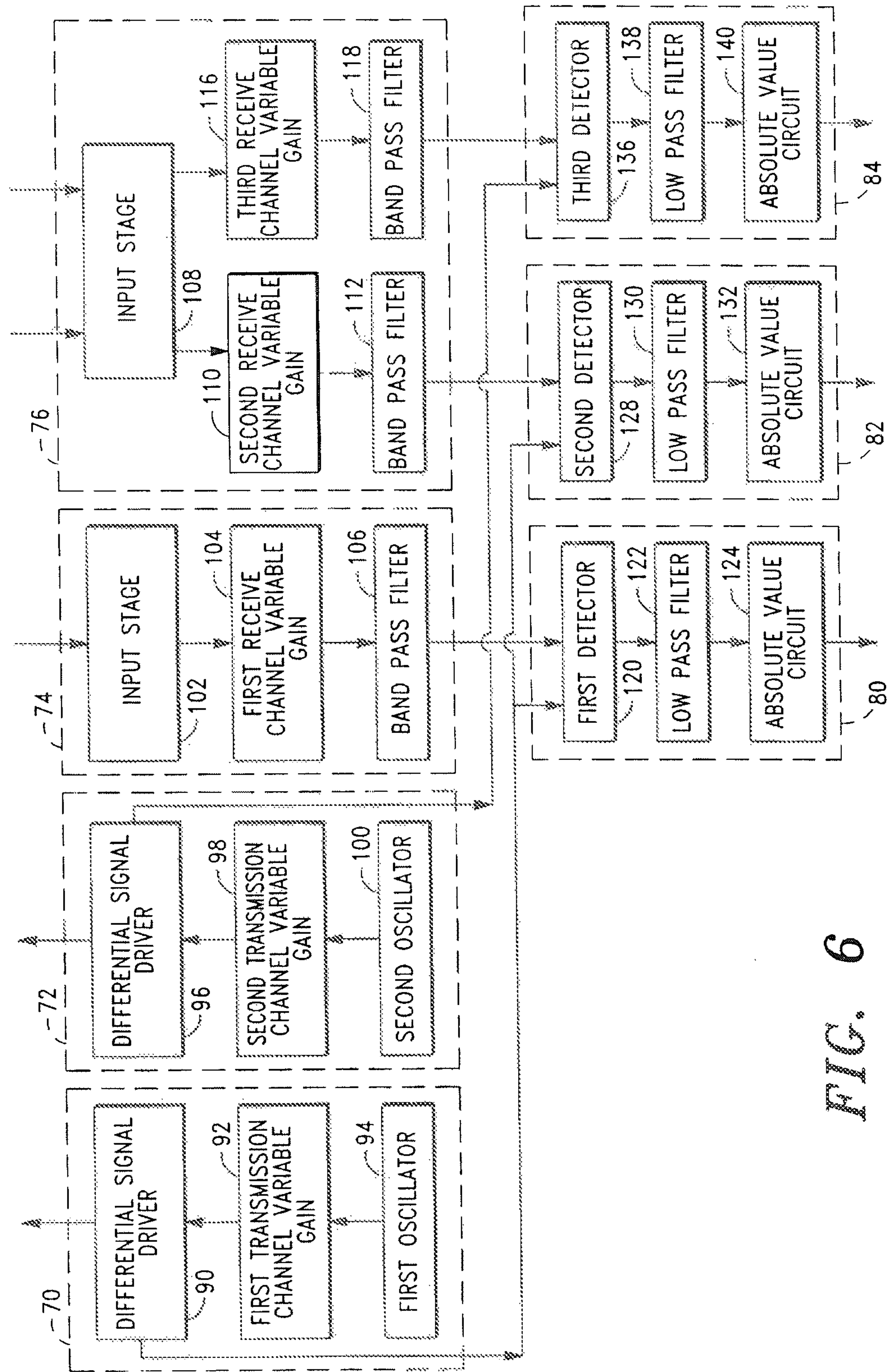
FIG. 6 is a further schematic illustration of the data acquisition circuitry shown in FIG. 4, according to the invention.

Referring now to FIG. 6, there is shown a more detailed view of selected components of the data acquisition circuitry 21, in accordance with one embodiment of the invention. As illustrated in FIG. 6, the data acquisition circuitry 21 includes a first transmission signal pre-processor 70 having a first oscillator 94. In one embodiment, the first oscillator 94 is set to 8.97 kHz.

According to the invention, the oscillator signal is transmitted to a first transmission channel variable gain circuit 92, which allows an optimal gain value to be set. The gain adjusted signal is then transmitted to a differential signal driver 90, and is then transmitted to the first transmission coil 60.

As illustrated in FIG. 6, the output from the differential signal driver 90 is also transmitted to the first channel detection circuitry 80 and the second channel detection circuitry 82, as will be discussed further below.

The second transmission signal-processor 72 operates in a similar manner. According to the invention, the second oscillator 100 oscillates at a pre-determined frequency, e.g., 7 kHz. The oscillator signal is transmitted to a second transmission channel variable gain circuit 98, which is independently set for an optimal gain value. The gain adjusted signal is then transmitted to a differential signal driver 96, and is then transmitted to the second transmission coil 62. The output of the differential signal driver 96 is also transmitted to the third channel detection circuitry 84, as will be discussed further below.

The signal from the first transmission coil 60 is processed by the first receive coil 61 and is then transmitted to the first received signal pre-processor 74. As illustrated in FIG. 6, the first signal pre-processor 74 can be implemented with an input stage 102, a first receive channel variable gain 104, and a band pass filter 106.

According to the invention, the variable gain 104 can be set through the data input interface circuitry 24 to optimize the signal-to-noise ratio. Preferably, the band pass filter 106 is set to reduce noise above and below 8.97 KHz.

The second received signal pre-processor 76 operates in a similar manner. However, as indicated above, the second receive coil 63 is preferably adapted to process two signals. The second received signal pre-processor 76 accordingly processes two signals.

As illustrated in FIG. 6, a single input stage 108 processes the two signals and transmits the output to two channels in communication with the input stage 108. Each channel includes a variable gain circuit 110/116 and a band pass filter 112/118.

According to the invention, the separate gain controls 92, 98, 104, 110, 116 are preferably optimized to increase the signal-to-noise ratio. The gain controls 92, 98 for the transmitted signal can also be optimized to minimize power requirements.

Since the gain for the transmitted signal can be changed independently of the gain of the receiver channel, the signal-to-noise ratio can be improved, while minimizing the magnetic field exposure at skin surface of the patient.

According to the invention, the band pass filters 106, 112, 118 are adapted to minimize interference from extraneous magnetic fields and noise sources. As illustrated in FIG. 6, the output from the first received signal preprocessor 74 is transmitted to the first channel detection circuitry 80. The circuitry 80 preferably includes a first detector 120, which is set to the frequency established by the first oscillator 94. The output of the first detector 120 is transmitted to a low pass filter 122 and an absolute value circuit 124. The signal is then transmitted to the data input interface circuitry 24 for processing by the CPU 28.

The second channel detection circuitry 82 operates in a similar manner. The second detector 128 is set to the frequency established by the first oscillator 94 and processes the signal from the second receive channel band pass filter 112. The second channel detection circuitry 82 includes a low pass filter 130 and an absolute value circuit 132 to produce a data signal that is also transmitted to the CPU 28 for processing, in accordance with the executable programs stored in memory 30.

The third channel detection circuitry 84 is set to the frequency established by the second oscillator 100 and processes the signal from the third receive channel band pass filter 118. The third receive channel detection circuitry 84 also includes a low pass filter 138 and an absolute value circuit 140.

Processing associated with the executable programs stored in memory 30 will now be described in detail.

According to the invention, the calibration program or routine 32 determines calibration coefficients, i.e. volume-motion coefficients, throughout a range of body positions and activities. Calibration coefficients are then derived for specific activities or body postures, i.e. sets of calibration coefficients. These different sets of calibration coefficients are then applied to selected regions of the acquired data set.

The calibration routine 32 thus allows the user to employ volume-motion coefficients from different segments of the data set (e.g., sitting, standing, walking, etc.). These coefficients can then be applied to the data set to construct spirograms of volume over time.

In some embodiments of the invention, the calibration program 32 is also adapted to "automatically" select derived volume-motion coefficients, i.e. a volume-motion coefficient data set, reflecting a specific body position (or posture) or activity when a subject or patient is in the noted body position or performing the activity. In the noted embodiments, the calibration program 32 would automatically select a volume-motion coefficient data set in response to a transmitted body posture-motion signal.

As will be appreciated by one having ordinary skill in the art, various sensors can be employed within the scope of the invention to sense and transmit the body posture-motion signal, e.g., 3-axis accelerometer. In one embodiment of the invention, the calibration program 32 is responsive to a signal reflecting the axial displacement of the chest wall, e.g., change in the sternal or xiphi-umbilical distance.

As discussed in detail in the Examples section, the calibration routine 32 facilitates the accurate determination of the volume of air inhaled and exhaled; the volume, i.e. $V_T$, being determined from the sum of three signals (the changes in the axial dimensions of the anteroposterior diameter of the rib cage (RC) and abdomen (Ab) and the changes in the axial dimensions of the anterior chest wall).

In accordance with one embodiment of the invention, the calibration maneuver includes having a subject breath through a flow meter, e.g., flow meter 86, for 1-2 minutes at varied tidal volumes and body positions.

In some embodiments of the invention, the calibration program 32 is also used to adjust the variable gain elements 92, 98, 104, 110, and 116 for optimum signal levels.

As indicated above, in one embodiment, the element analysis program 36 is adapted to perform element analyses on acquired signals (representing acquired data) to reduce any extraneous noise in the signals. In one embodiment of the invention, the element analyses includes at least one Fourier analysis, which, combined with band pass filtering in the software, facilitates use of the system 20A in ambulatory activities.

In one embodiment of the invention, the ventilation parameter program 38 correlates the "three-degrees-of-freedom" data with the flow meter data. The parameter program 38 then employs the data to create correlation parameters for determining ventilation parameters or characteristics, including end-expiratory, lung volume, breathing frequency, total pulmonary ventilation, inspiratory breathing time, expiratory breathing time, and total breathing time. These parameters can then be displayed on an integral visual output device or transmitted wirelessly to an external receiver and/or display device.

Figure 7:
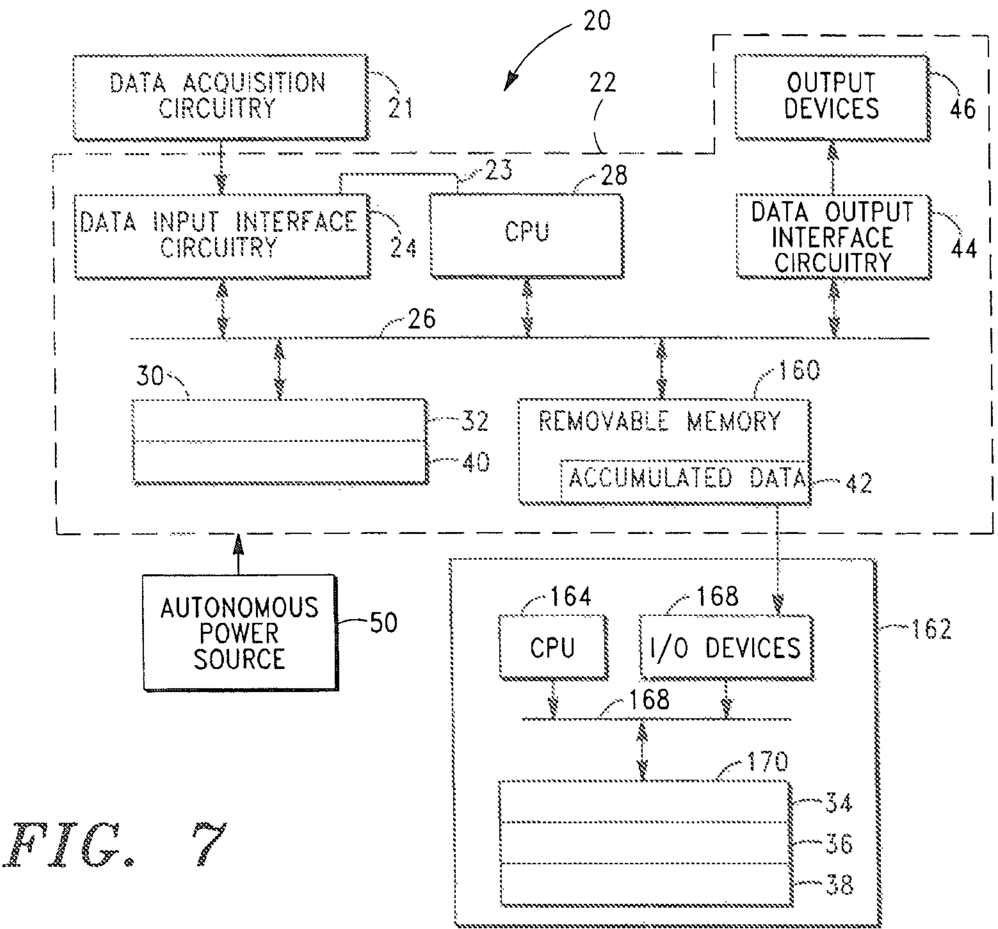
FIG. 7 is a schematic illustration of another embodiment of a pulmonary ventilation system, according to the invention.

Referring now to FIG. 7, there is shown another embodiment of the pulmonary ventilation system 20B of the invention. As illustrated in FIG. 7, the system 20B is similar to system 20A. However, in this embodiment the power source 50 is external to the data processing circuitry 22. Further, the pulmonary ventilation system 20B includes a removable memory 160 (e.g., a flash memory card), which is employed to store the accumulated data 42. The accumulated data can then be transferred to a receiving station, such as a personal computer 162.

In the illustrated embodiment, the personal computer 162 includes a central processing unit 164 and a set of input/output devices 166, which communicate via bus 168. The system 20B also includes memory medium 170, which is in communication with bus 168. As illustrated in FIG. 7, the memory medium 162 includes the element analysis program, ventilation parameter program and digital band pass filters 34.

As will be readily appreciated by one having ordinary skill in the art, system 20B facilitates processing of the accumulated data 42 with a separate device.

EXAMPLES

The following examples are given to enable those skilled in the art to more clearly understand and practice the present invention. They should not be considered as limiting the scope of the invention, but merely as being illustrated as representative thereof.

Example 1

Subjects

Thirty (30) subjects were selected to assess the accuracy of the "three-degrees-of-freedom" model of the invention. As reflected in Table 1, ten (10) healthy subjects with no known history of sleep-disordered breathing and ten (10) obese subjects were studied while awake in the supine, right and left lateral decubitus positions. Ten (10) obese subjects with obstructive sleep apnea (obese sleeping subjects) were studied while unrestrained during a daytime nap.

TABLE 1

| Subject | Non-Obese Awake Subjects (BMI) | Obese Awake Subjects (BMI) | Obese Subjects Daytime Nap$^+$ (BMI) |
|---|---|---|---|
| 1 | 20 | 52 | 51 |
| 2 | 30 | 45 | 61 |
| 3 | 27 | 61 | 49 |
| 4 | 28 | 49 | 40 |
| 5 | 27 | 59 | 34 |
| 6 | 29 | 40 | 38 |
| 7 | 23 | 34 | 51 |
| 8 | 27 | 38 | 39 |
| 9 | 21 | 50 | 56 |
| 10 | 25 | 39 | 38 |
| Mean ± SD | 25.7 ± 3.4 | 46.7 ± 9.1 | 45.7 ± 1.0 |

BMI: Body Mass Index

The non-obese, awake subjects comprised seven (7) males and three (3) females, age 28-49 yr. (mean age 30.2 yr). The obese, awake subjects comprised six (6) males and four (4) females, age 24-64 yr. (mean age 44.4 yr). The obese, napping subjects comprised five (5) males and five (5) females, age 28-60 yr. (mean age 42.2 yr).

Device and Measurements

The anteroposterior displacements of the rib cage and abdomen, as well as the axial displacements of the chest wall (i.e. Xi) were measured using a light-weight, portable pulmonary ventilation system of the invention (also referred to herein as a magnetometer system or device) using the "three-degrees-of-freedom" model set forth in Eq. 5 above. Signals were sampled at 20 Hz and stored to compact flash memory.

Calibration was performed with subjects in the supine, right lateral and left lateral decubitus positions, as set forth in Paek, et al., "Postural Effects on Measurements of Tidal Volume From Body Surface Displacements", J. Appl. Physiol., vol. 68, pp. 2482-2487 (1990); which is expressly incorporated by reference herein.

Protocol

The non-obese and obese awake subjects were studied while in the supine, right lateral and left lateral decubitus positions (hereinafter "test positions"). After calibration, each subject breathed through a mouthpiece connected to a spirometer (PK Morgan Ltd®). Subjects were instructed to take breaths ranging from 0.5 to 2.5 L. At least 15 breaths (average 25.6 breaths) of varied volumes were obtained from each subject in each position. Data was simultaneously collected using a ventilation or magnetometer system of the invention, such as system 20B described above.

The daytime nap studies were done using a tight-fitting facemask equipped with a pneumotachograph applied to cover the nose and mouth. Subjects were observed while sleeping in a quiet room. Each subject was monitored continuously and changes in position were recorded. Data was collected simultaneously using the magnetometer system.

Statistical Analysis

The coefficient of determination ($R^2$) was calculated for $V_T$, $T_I$, and $T_E$ derived from the simultaneous spirometer or pneumotachograph and magnetometer signals using a linear correlation model. This analysis was performed for individual subjects in each position and for pooled data from all subjects in all positions. The mean percent differences (% difference) between the spirometer or pneumotachograph and magnetometer derived measurements ($V_T$, $T_I$ and $T_E$) were also calculated.

Both absolute and mathematical differences were calculated and used to assess correlation and agreement (see below). $T_I$ and $T_E$ correlations were calculated for the daytime nap studies using 65 randomly selected breaths from each study.

The methods set forth in Bland, et al., "*Statistical Methods for Assessing Agreement Between the Two Methods of Clinical Measurement*", Lancet, vol. 1, pp. 307-310 (1986), which is incorporated by reference herein, were used to assess the agreement between measurements obtained from the spirometer and magnetometer or pneumotachograph and magnetometer.

Results

As discussed in detail below, there were significant correlations between the spirometer and magnetometer measurements of $V_T$, $T_I$ and $T_E$ during wakefulness for the non-obese and obese subjects. For the non-obese awake subjects (n=10), the $R^2$ values for $V_T$, $T_I$, and $T_E$ for each subject in each of the test positions were determined (see Tables 2 and 3A and 3B below):

TABLE 2

| Non-Obese Awake Subjects | | | Obese Awake Subjects | | |
|---|---|---|---|---|---|
| Subject | Mean % Diff* ± SD | $R^2$ | Subject | Mean % Diff* ± SD | $R^2$ |
| 1 | 12.2 ± 12% | 0.94 | 11 | 8.7 ± 7% | 0.96 |
| 2 | 8.1 ± 8% | 0.97 | 12 | 9.7 ± 7% | 0.94 |
| 3 | 7.5 ± 6% | 0.97 | 13 | 6.6 ± 3% | 0.98 |
| 4 | 10.2 ± 9% | 0.95 | 14 | 13.8 ± 7% | 0.84 |
| 5 | 11.8 ± 9% | 0.90 | 15 | 12.3 ± 9% | 0.91 |
| 6 | 7.6 ± 7% | 0.98 | 16 | 7.0 ± 4% | 0.98 |
| 7 | 13.5 ± 9% | 0.90 | 17 | 8.8 ± 6% | 0.92 |
| 8 | 12.1 ± 8% | 0.97 | 18 | 6.4 ± 4% | 0.97 |
| 9 | 13.8 ± 9% | 0.87 | 19 | 7.3 ± 6% | 0.94 |
| 10 | 10.5 ± 6% | 0.92 | 20 | 10.5 ± 11% | 0.92 |
| Mean ± SD | 10.6 ± 9% | 0.94 | Mean ± SD | 9.0 ± 7% | 0.95 |

*Absolute differences

TABLE 3A

| Non-Obese Awake Subjects | | | | |
|---|---|---|---|---|
| | $T_1$ | | $T_2$ | |
| Subject | Mean % Diff* ± SD | $R^2$ | Mean % Diff* ± SD | $R^2$ |
| 1 | 11.4 ± 11% | 0.86 | 8.5 ± 9% | 0.87 |
| 2 | 9.3 ± 9% | 0.72 | 8.0 ± 7% | 0.83 |
| 3 | 8.1 ± 4% | 0.89 | 9.2 ± 4% | 0.91 |
| 4 | 10.5 ± 8% | 0.61 | 10.6 ± 8% | 0.78 |
| 5 | 5.7 ± 5% | 0.96 | 7.4 ± 6% | 0.89 |
| 6 | 9.6 ± 9% | 0.84 | 7.3 ± 6% | 0.92 |
| 7 | 12.7 ± 9% | 0.89 | 8.5 ± 5% | 0.97 |

TABLE 3A-continued

| Non-Obese Awake Subjects | | | | |
|---|---|---|---|---|
| | $T_1$ | | $T_2$ | |
| Subject | Mean % Diff* ± SD | $R^2$ | Mean % Diff* ± SD | $R^2$ |
| 8 | 15.0 ± 14% | 0.83 | 9.0 ± 7% | 0.95 |
| 9 | 6.5 ± 7% | 0.87 | 7.6 ± 7% | 0.88 |
| 10 | 10.8 ± 8% | 0.88 | 9.7 ± 8% | 0.87 |
| Mean ± SD | 9.7 ± 9% | 0.88 | 8.6 ± 8% | 0.91 |

TABLE 3B

| Obese Awake Subjects | | | | |
|---|---|---|---|---|
| | $T_1$ | | $T_2$ | |
| Subject | Mean % Diff* ± SD | $R^2$ | Mean % Diff* ± SD | $R^2$ |
| 11 | 9.5 ± 9% | 0.88 | 6.3 ± 6% | 0.93 |
| 12 | 8.5 ± 8% | 0.77 | 7.5 ± 6% | 0.90 |
| 13 | 7.2 ± 6% | 0.87 | 7.4 ± 7% | 0.90 |
| 14 | 3.5 ± 3% | 0.91 | 3.6 ± 3% | 0.96 |
| 15 | 8.4 ± 7% | 0.87 | 7.7 ± 6% | 0.83 |
| 16 | 5.4 ± 5% | 0.91 | 5.4 ± 5% | 0.95 |
| 17 | 6.4 ± 5% | 0.80 | 5.7 ± 6% | 0.89 |
| 18 | 8.3 ± 7% | 0.94 | 5.0 ± 5% | 0.97 |
| 19 | 8.1 ± 6% | 0.92 | 7.5 ± 6% | 0.97 |
| 20 | 5.9 ± 4% | 0.91 | 4.8 ± 3% | 0.95 |
| Mean ± SD | 7.5 ± 7% | 0.96 | 6.4 ± 6% | 0.97 |

*Absolute differences

Figure 8A:
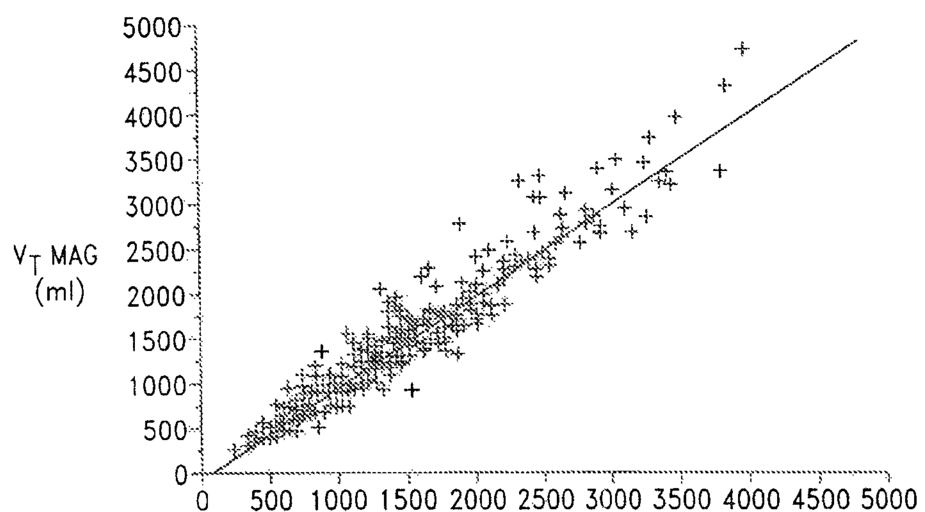
FIG. 8A is a graphical illustration of magnetometer derived volume vs. spirometer derived volume for non-obese subjects in three different sleep positions, i.e. supine, right and left lateral decubitus positions, according to the invention.
Figure 8B:
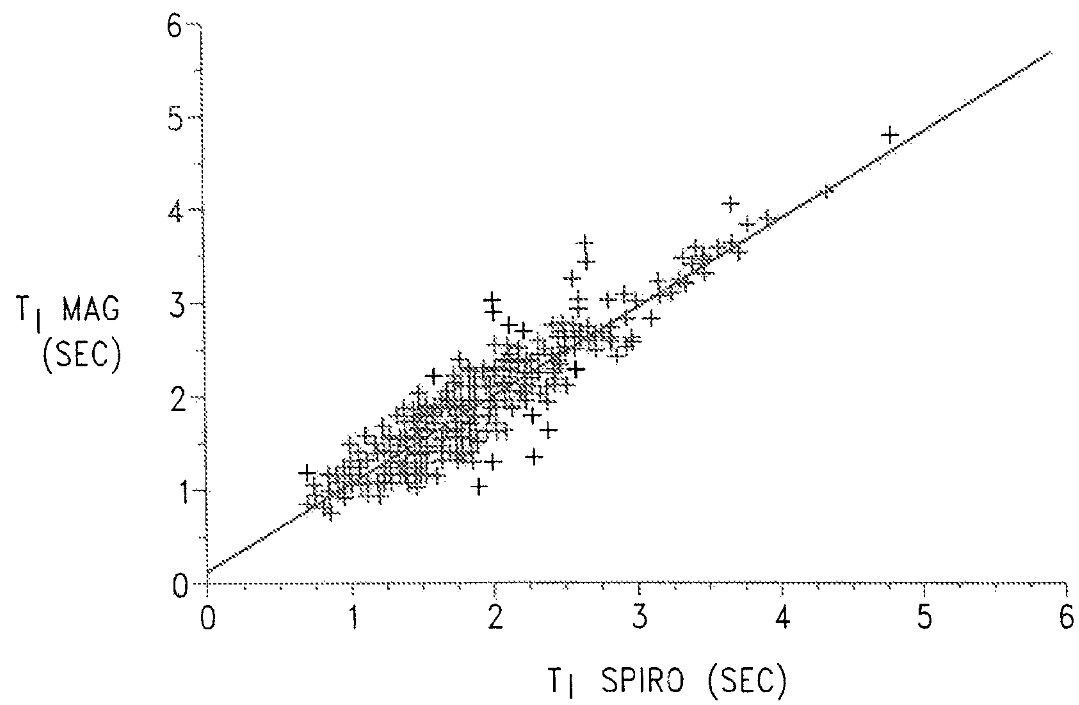
FIG. 8B is a graphical illustration of magnetometer derived inspiratory time vs. spirometer derived inspiratory time for non-obese subjects in supine, right and left lateral decubitus positions, according to the invention.
Figure 8C:
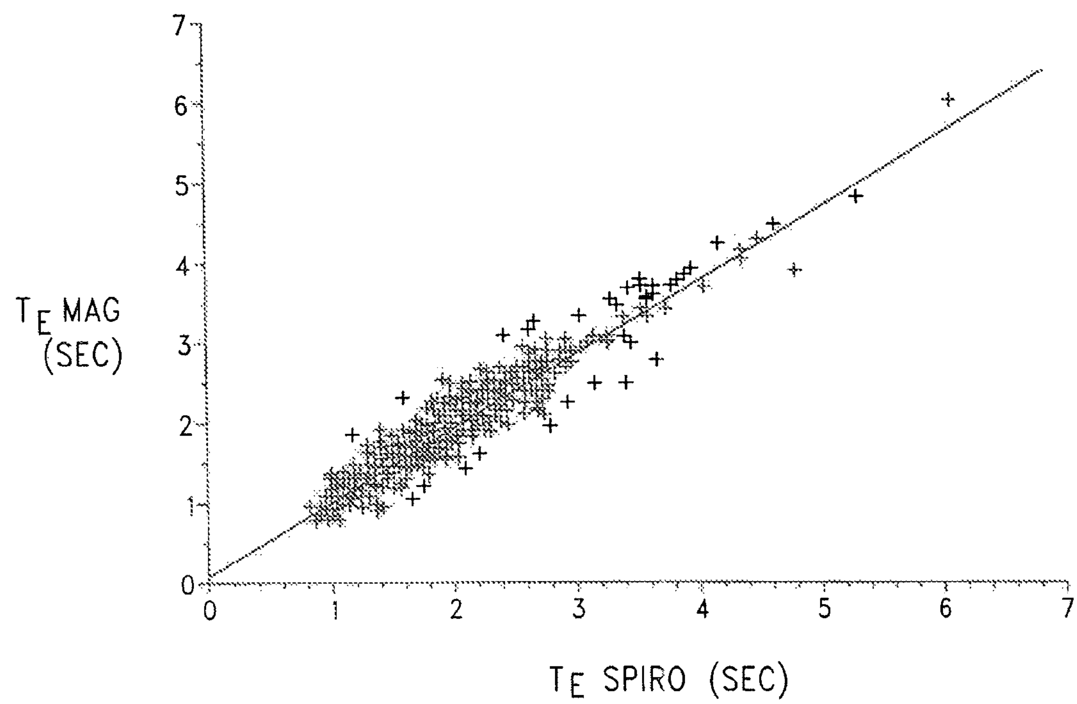
FIG. 8C is a graphical illustration of magnetometer derived expiratory time vs. spirometer derived expiratory time for non-obese subjects in supine, right and left lateral decubitus positions, according to the invention.

For pooled data of all subjects in all test positions, a total of 645 breaths were analyzed. The $R^2$ values for $V_T$, $T_I$ and $T_E$ were 0.94, 0.88, and 0.91, respectively (see FIGS. 8A, 8B, and 8C).

The absolute mean % differences for $V_T$, $T_I$ and $T_E$ for each subject in each of the test positions are also shown in Tables 2, 3A and 3B. As reflected in Tables 2, 3A and 3B, the absolute mean % differences for $V_T$, $T_I$ and $T_E$ from pooled data were 10.6±9%, 9.7±9%, and 8.6±8% (means±SD), respectively.

For the obese awake subjects (n=10), similar results were obtained. The $R^2$ values for $V_T$, $T_I$ and $T_E$ were similarly determined and are set forth in Tables 2 and 3.

Figure 9A:
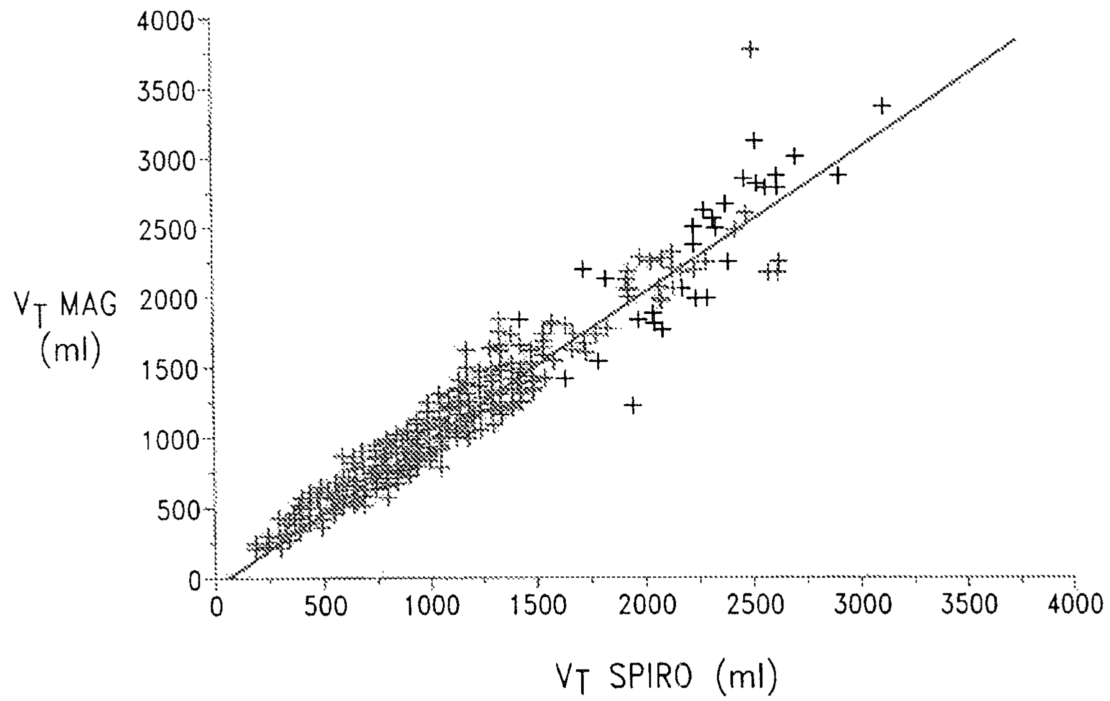
FIG. 9A is a graphical illustration of magnetometer derived volume vs. spirometer derived volume for awake obese subjects in supine, right and left lateral decubitus positions, according to the invention.
Figure 9B:
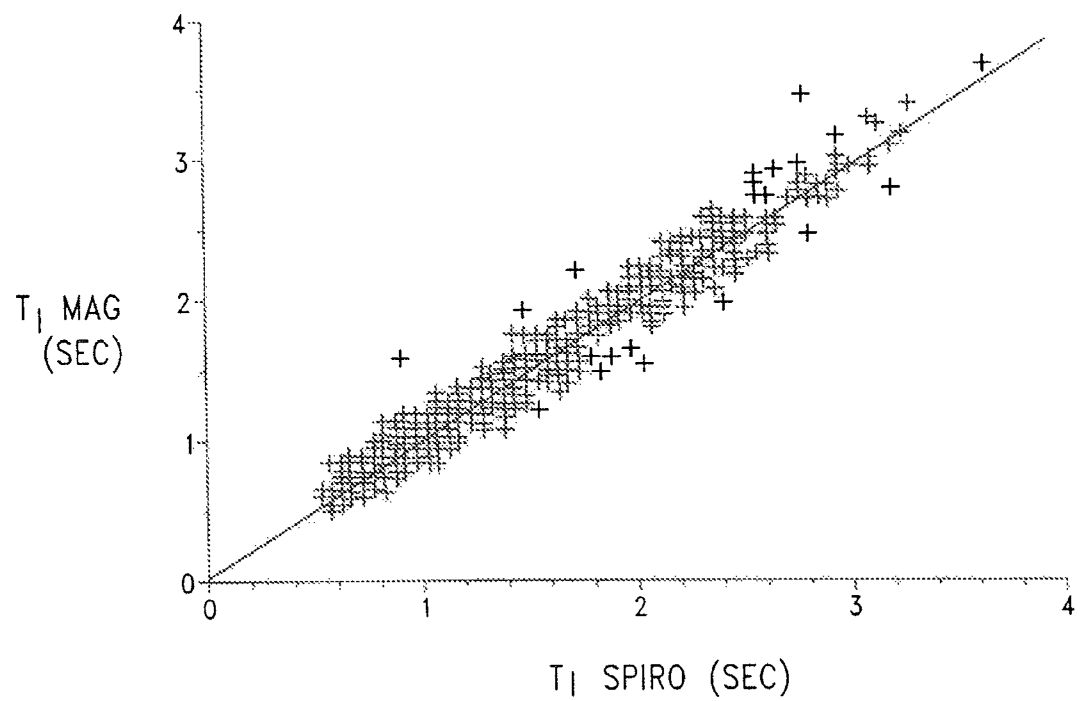
FIG. 9B is a graphical illustration of magnetometer derived inspiratory time vs. spirometer derived inspiratory time for awake obese subjects in supine, right and left lateral decubitus positions, according to the invention.
Figure 9C:
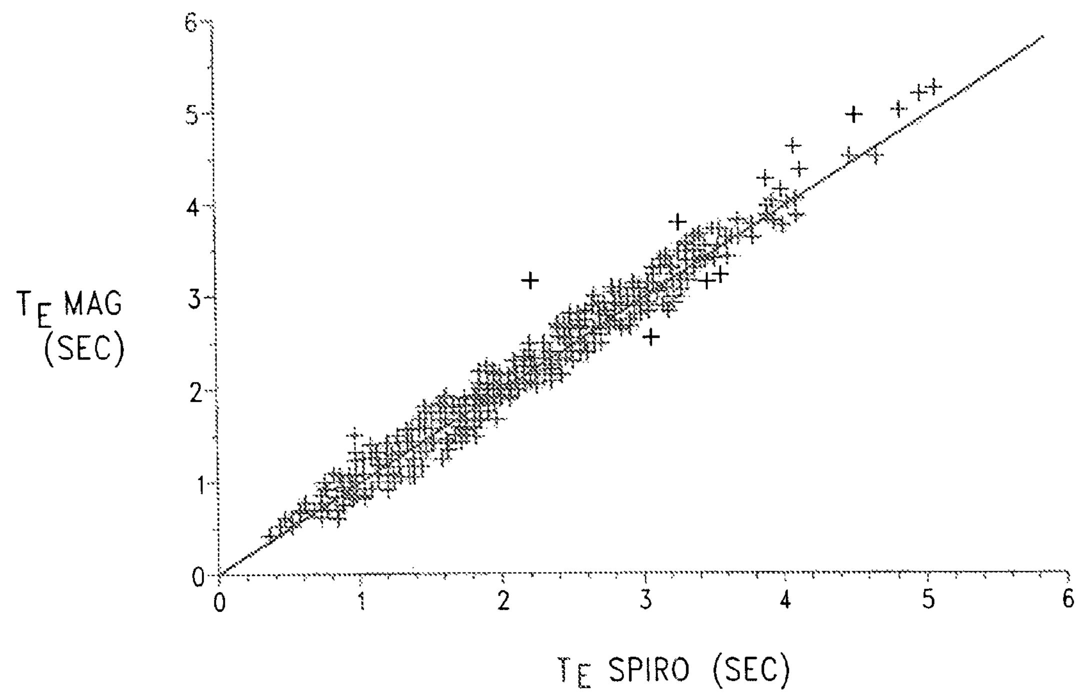
FIG. 9C is a graphical illustration of magnetometer derived expiratory time vs. spirometer derived expiratory time for awake obese subjects in supine, right and left lateral decubitus positions, according to the invention.

For pooled data of all subjects in all positions, a total of 892 breaths were analyzed. The $R^2$ values for $V_T$, $T_I$, and $T_E$ were 0.95, 0.96, and 0.97, respectively (see FIGS. 9A, 9B, and 9C).

The absolute mean % differences for $V_T$, $T_I$ and $T_E$ for each subject in each of the test positions are similarly shown in Tables 2 and 3. As also reflected in Tables 2, 3A and 3B, absolute mean % differences for $V_T$, $T_I$ and $T_E$ from pooled data were 9.0±7%, 7.5±7%, and 6.4±6% (mean±SD), respectively.

There were also significant correlations between the pneumotachograph and the magnetometer measurements during daytime sleep for the obese subjects. The $R^2$ values for $V_T$, $T_I$ and $T_E$ for each of the obese sleeping subjects were determined and are set forth in Table 4 below.

TABLE 4

| Obese Subjects During Daytime Nap | | | | | | |
|---|---|---|---|---|---|---|
| | $V_T$ | | $T_I$ | | $T_E$ | |
| Subject | Mean % Diff* % SD | $R^2$ | Mean % Diff* % SD | $R^2$ | Mean % Diff* % SD | $R^2$ |
| 21 | 9.1 ± 8% | 0.93 | 13.5 ± 7% | 0.88 | 7.6 ± 4% | 0.94 |
| 22 | 6.2 ± 5% | 0.92 | 11.2 ± 14% | 0.89 | 10.3 ± 7% | 0.90 |
| 23 | 5.7 ± 5% | 0.80 | 7.1 ± 7% | 0.92 | 5.2 ± 4% | 0.84 |
| 24 | 15.8 ± 12% | 0.87 | 7.1 ± 5% | 0.95 | 5.3 ± 4% | 0.98 |
| 25 | 8.9 ± 7% | 0.91 | 6.4 ± 5% | 0.95 | 6.5 ± 5% | 0.90 |
| 26 | 7.6 ± 6% | 0.96 | 7.2 ± 6% | 0.96 | 5.8 ± 5% | 0.97 |
| 27 | 13.9 ± 11% | 0.81 | 9.9 ± 6% | 0.94 | 6.8 ± 5% | 0.97 |
| 28 | 5.6 ± 4% | 0.89 | 9.6 ± 7% | 0.94 | 6.4 ± 4% | 0.95 |
| 29 | 12.2 ± 9% | 0.93 | 8.9 ± 6% | 0.87 | 7.4 ± 5% | 0.95 |
| 30 | 10.8 ± 10% | 0.73 | 8.5 ± 6% | 0.89 | 5.1 ± 4% | 0.90 |
| Mean ± SD | 9.1 ± 8% | 0.94 | 8.9 ± 8% | 0.95 | 6.6 ± 5% | 0.95 |

*Absolute differences

Figure 10A:
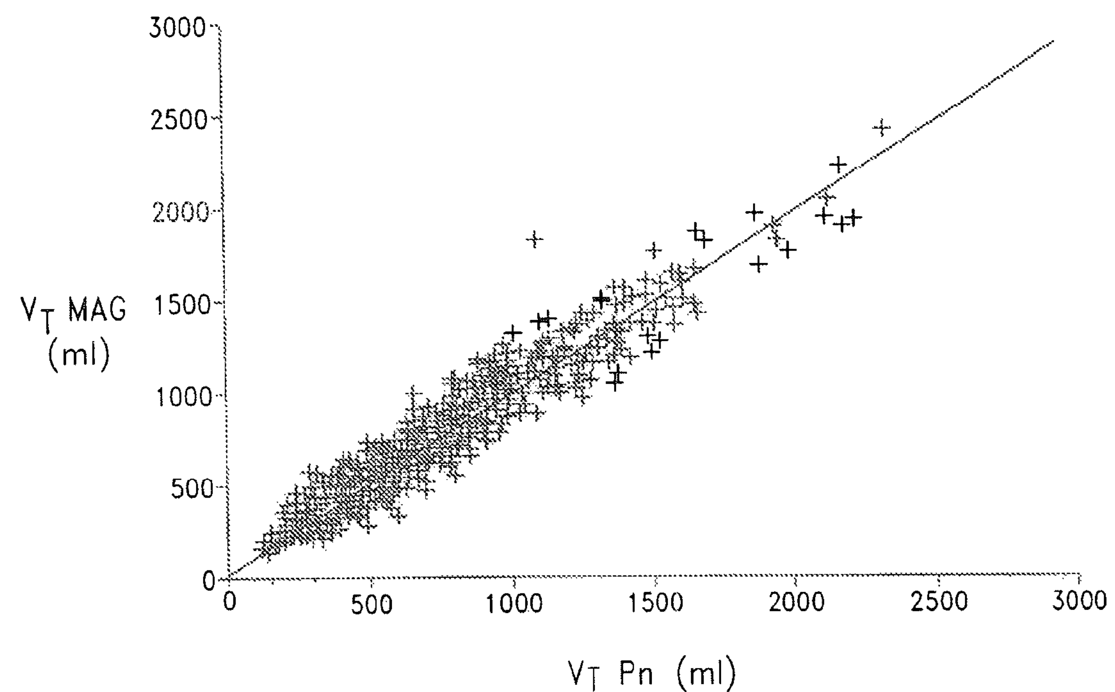
FIG. 10A is a graphical illustration of magnetometer derived volume vs. pneumotachograph derived volume for obese subjects in supine, right and left lateral decubitus positions during a day-time nap, according to the invention.
Figure 10B:
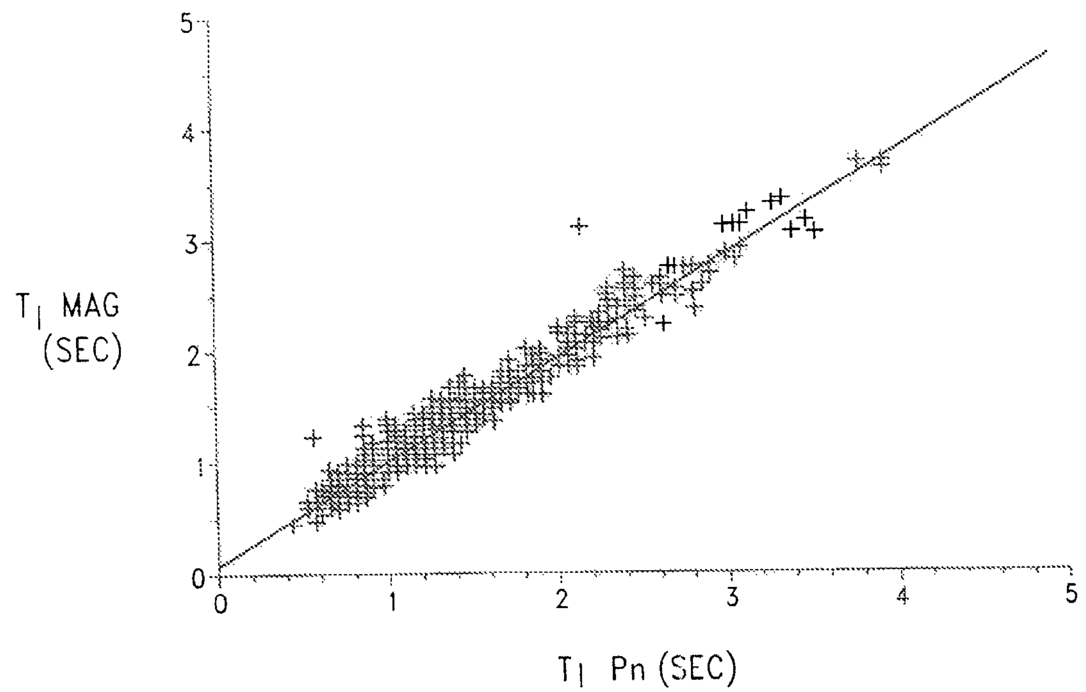
FIG. 10B is a graphical illustration of magnetometer derived inspiratory time vs. pneumotachograph derived inspiratory time for obese subjects in supine, right and left lateral decubitus positions during a day-time nap, according to the invention.
Figure 10C:
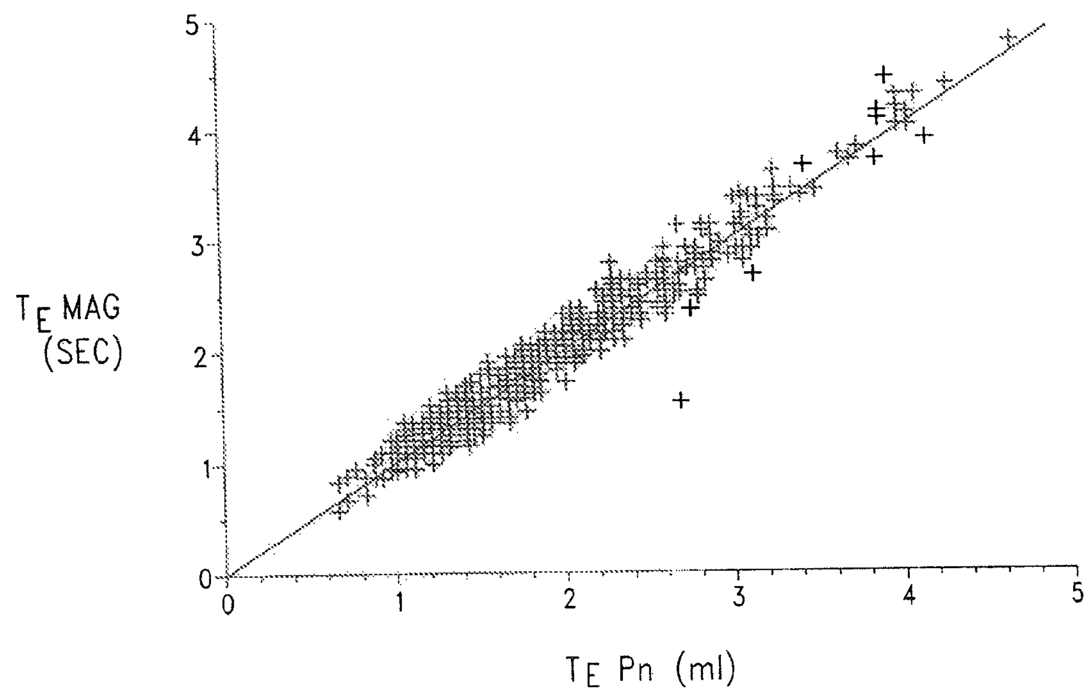
FIG. 10C is a graphical illustration of magnetometer derived expiratory time vs. pneumotachograph derived expiratory time for obese subjects in supine, right and left lateral decubitus positions during a day-time nap, according to the invention.

For $V_T$, a total of 3861 breaths were analyzed. For $T_I$ and $T_E$, 65 randomly selected breaths were analyzed from each subject (n=650 breaths). The $R^2$ values for $V_T$, $T_I$ and $T_E$ were 0.94, 0.95, and 0.95, respectively (see FIGS. 10A, 10B, and 10C).

The absolute mean % differences for $V_T$, $T_I$, and $T_E$ for individual subjects are also shown in Table 4. As reflected in Table 4, the absolute mean % differences for $V_T$, $T_I$ and $T_E$ from pooled data were 9.1±8%, 8.9±8%, and 6.6±5%, respectively.

Figures 11A, 11B:
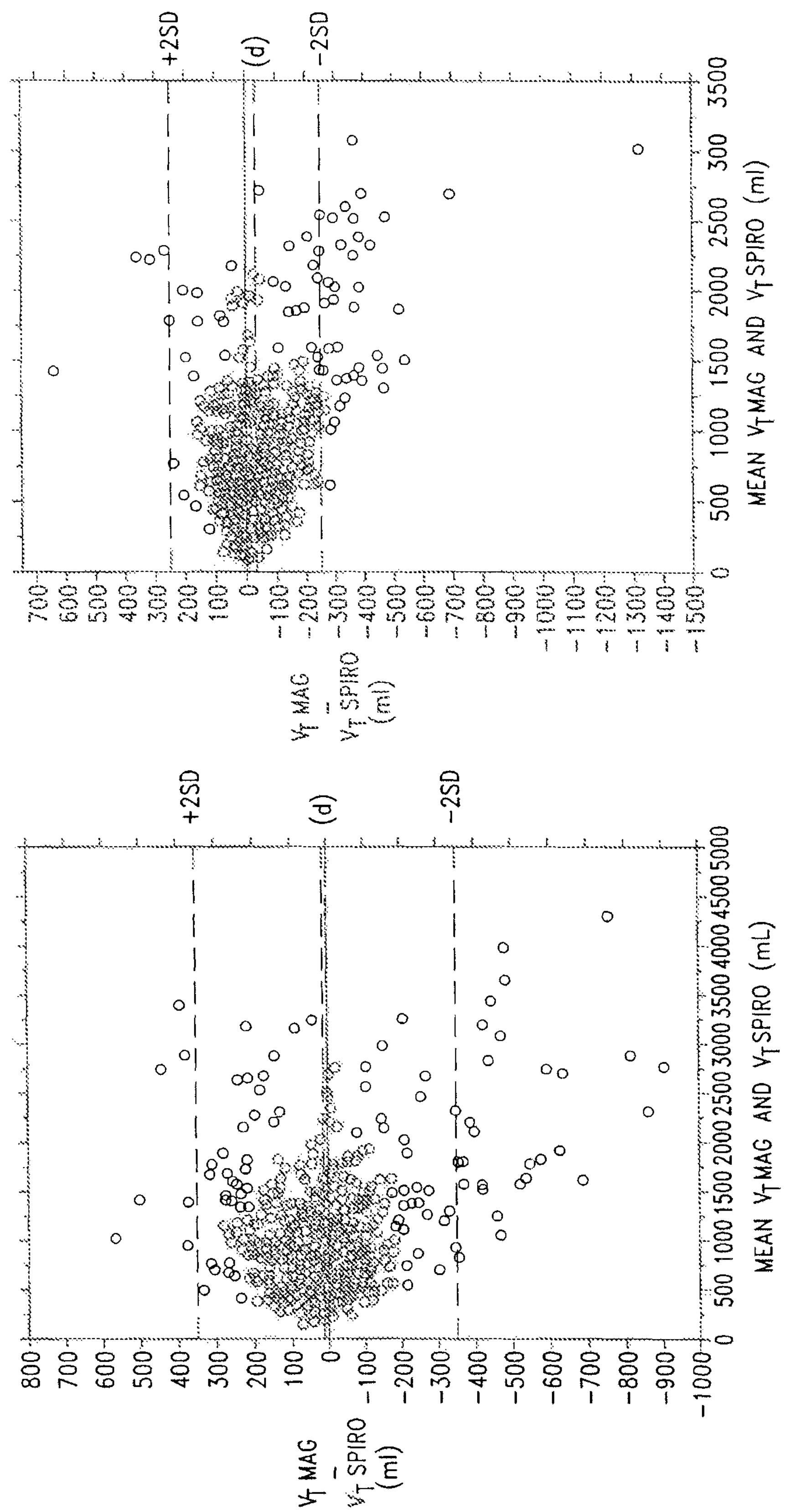
FIG. 11A is a graphical illustration of magnetometer and spirometer derived volumes vs. mean magnetometer and spirometer derived volumes for awake non-obese subjects, according to the invention.
FIG. 11B is a graphical illustration of magnetometer and spirometer derived volumes vs. mean magnetometer and spirometer derived volumes for awake obese subjects, according to the invention.

Using the Bland, et al. methods, agreement between the magnetometer and spirometer or pneumotachograph values for $V_T$ ($V_{T\,Mag}$ and $V_{T\,Spiro}$ or $V_{T\,Pn}$), $T_I$ ($T_{I\,Mag}$ and $T_{I\,Spiro}$ or $T_{I\,Pn}$), and $T_E$ ($T_{E\,Mag}$ and $T_{E\,Spiro}$ or $T_{E\,Pn}$) for subjects in the above different groups was assessed. The mathematical mean differences (d) between $V_{T\,Spiro}$ and $V_{T\,Mg}$, and the 95% confidence intervals (reflecting bias) for the awake non-obese and obese subjects are graphically illustrated in FIGS. 11A and 11B.

Figure 12:
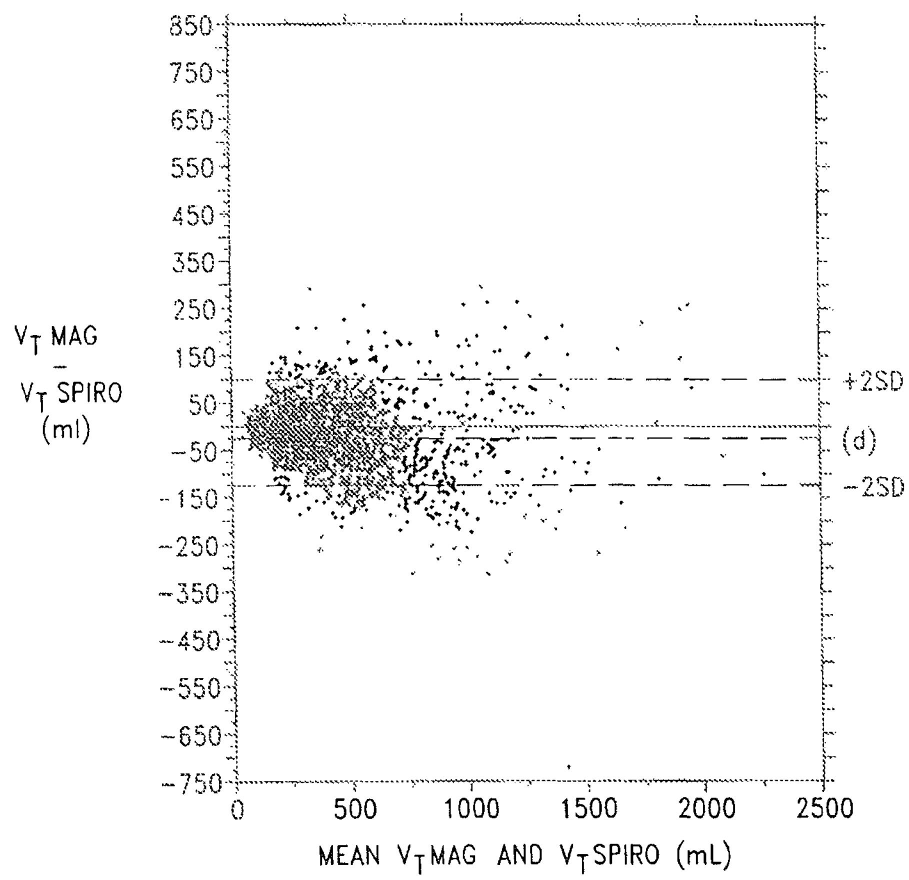
FIG. 12 is a graphical illustration of magnetometer and spirometer derived volumes vs. mean magnetometer and spirometer derived volumes for obese subjects during day-time sleep, according to the invention.

A similar graphical illustration for the obese sleeping subjects using the $V_{T\,Mag}$ and $V_{T\,Pn}$ data is shown in FIG. 12.

The mathematical mean difference for the non-obese awake subjects in all positions was 26.4 ml with a standard error (SE) of 6.8 ml. The means for $V_{T\,Spiro}$ and $V_{T\,Mag}$ for this data set were 1177.3 ml and 1150.9 ml, respectively.

For the obese awake subjects, the mathematical mean difference was −13.5 ml with a SE of 4.0 ml. The means for $V_{T\,Spiro}$ and $V_{T\,Mag}$ for this data set were 868.0 ml and 881.5 ml, respectively.

The mathematical mean difference between $V_{T\,Pn}$ and $V_{T\,Mag}$ for the obese sleeping subjects was −17.7 ml with a SE of 1.0 ml. Mean $V_{T\,Pn}$ and $V_{T\,Mag}$ for this group were 460.7 ml and 478.4 ml, respectively.

The limits of agreement (mean±95% confidence intervals) are shown in Table 5 below.

TABLE 5

| Group | | Magnetometer Mean | Mean Diff (d) ± SD | Limits of Agreement (d) ± 95% CI |
|---|---|---|---|---|
| Non-Obese | $V_T$ (ml) | 1150.9 | 26.4 ± 173.0 | −319.6 to +372.4 |
| Awake | $T_I$ (sec) | 1.80 | −0.06 ± 0.20 | −0.46 to +0.34 |
| Subjects | $T_E$ (sec) | 1.93 | +0.06 ± 0.20 | −0.34 to +0.46 |
| Obese | $V_T$ (ml) | 881.5 | −13.5 ± 119.0 | −251.5 to +224.5 |
| Awake | $T_I$ (sec) | 1.45 | −0.03 ± 0.12 | −0.27 to +0.21 |
| Subjects | $T_E$ (sec) | 1.76 | +0.02 ± 0.13 | −0.24 to +0.28 |
| Obese | $V_T$ (ml) | 478.4 | −17.7 ± 59.5 | −136.7 to +101.3 |

TABLE 5-continued

| Group | | Magnetometer Mean | Mean Diff (d) ± SD | Limits of Agreement (d) ± 95% CI |
|---|---|---|---|---|
| Subjects | $T_I$ (sec) | 1.39 | +0.001 ± 0.14 | −0.28 to +0.28 |
| During | $T_E$ (sec) | 1.92 | +0.003 ± 0.15 | −0.30 to +0.30 |
| Daytime | | | | |
| Nap | | | | |

(d): Mathematical differences
CI: Confidence Intervals

The limits of agreement for $T_I$ and $T_E$ during wakefulness and sleep are also summarized in Table 5. It can be seen that the limits of agreement for $V_T$ are clinically acceptable (e.g. ±20-30% of $V_T$). As evidenced by the graphical illustrations shown in FIGS. 11A, 11B and 12, most of the data is aggregated around zero with a minor percentage scattered peripherally. This scattering of data over the higher ranges of $V_T$ increases the limits of agreement.

This peripheral scatter is primarily due to three factors. First, the range of $V_T$ studied was wide during wakefulness (e.g., for group 1, $V_T$ ranged from 250 to 4100 ml), as the subjects were instructed to take occasional deep breaths. The inaccuracies over this range of volume may be due to the lesser range of $V_T$ encountered during sleep.

Second, some of the measurements that were scattered peripherally may represent accidental manual errors in measurements from the spirometer or pneumotachograph. Third, the effect of the facemask on $V_T$ may have increased $V_T$ in our sleeping subjects.

Nonetheless, as will be appreciated by one having ordinary skill in the art, the agreements and bias are accurate enough to be clinically relevant.

Example 2

Subjects

The following study was conducted to assess the accuracy of the "three-degrees-of-freedom" model of the invention and a pulmonary ventilation or magnetometer system employing the subject model to detect apneas and hypopneas during sleep.

As reflected in Table 6, fifteen (15) subjects (10 males and 5 females) with variable degrees of clinical suspicion for obstructive sleep apnea (OSA) were selected for the study. The mean age for the group was 45.47±12.5 years (mean±SD). The mean body mass index for the group was 35.00±5.7 kg/m$^2$.

TABLE 6

| Subject | Age | Body Mass Index (BMI) |
|---|---|---|
| 1 | 50 | 32 |
| 2 | 71 | 28 |
| 3 | 34 | 33 |
| 4 | 39 | 31 |
| 5 | 30 | 36 |
| 6 | 48 | 41 |
| 7 | 40 | 29 |
| 8 | 49 | 28 |
| 9 | 74 | 43 |
| 10 | 34 | 39 |
| 11 | 44 | 34 |
| 12 | 38 | 33 |
| 13 | 39 | 46 |

TABLE 6-continued

| Subject | Age | Body Mass Index (BMI) |
|---|---|---|
| 14 | 46 | 41 |
| 15 | 46 | 31 |
| Mean ± SD | 35.00 ± 5.7 | 45.47 ± 12.5 |

Device and Measurements

The anteroposterior displacements of the rib cage and abdomen, as well as the axial displacements of the chest wall (i.e. Xi) were similarly measured using a light-weight, portable pulmonary ventilation system of the invention (also referred to herein as a magnetometer system or device) using the "three-degrees-of-freedom" model set forth in Eq. 5 above.

Two pairs of electromagnetic coils, each ~½" in diameter, were employed to measure three degrees of chest wall motion. The coils were attached as shown in FIG. 3.

Signals were sampled at 20 Hz and stored to compact flash memory. A pneumotachograph was also attached to the magnetometer system for calibration.

Calibration was performed with subjects in the supine, right lateral and left lateral decubitus positions. Each subject was instructed to breath through the pneumotachograph with breaths of varied depth for greater than 1 min. Free movements of the upper and lower extremities were also encouraged during the calibration process (i.e. flexion and extension of the hip, knee, elbow and shoulder joints).

Multiple linear regression of the change in each chest wall dimension, with the corresponding tidal volume integrated from the pneumotachograph, was performed to obtain the volume-motion coefficients of Eq. 5.

Protocol

After calibration in the supine, right lateral and left lateral decubitus positions (hereinafter "test positions"), continuous recording of the magnetometer signals was performed throughout a 12 lead polysomnography (PSG).

Figure 13:
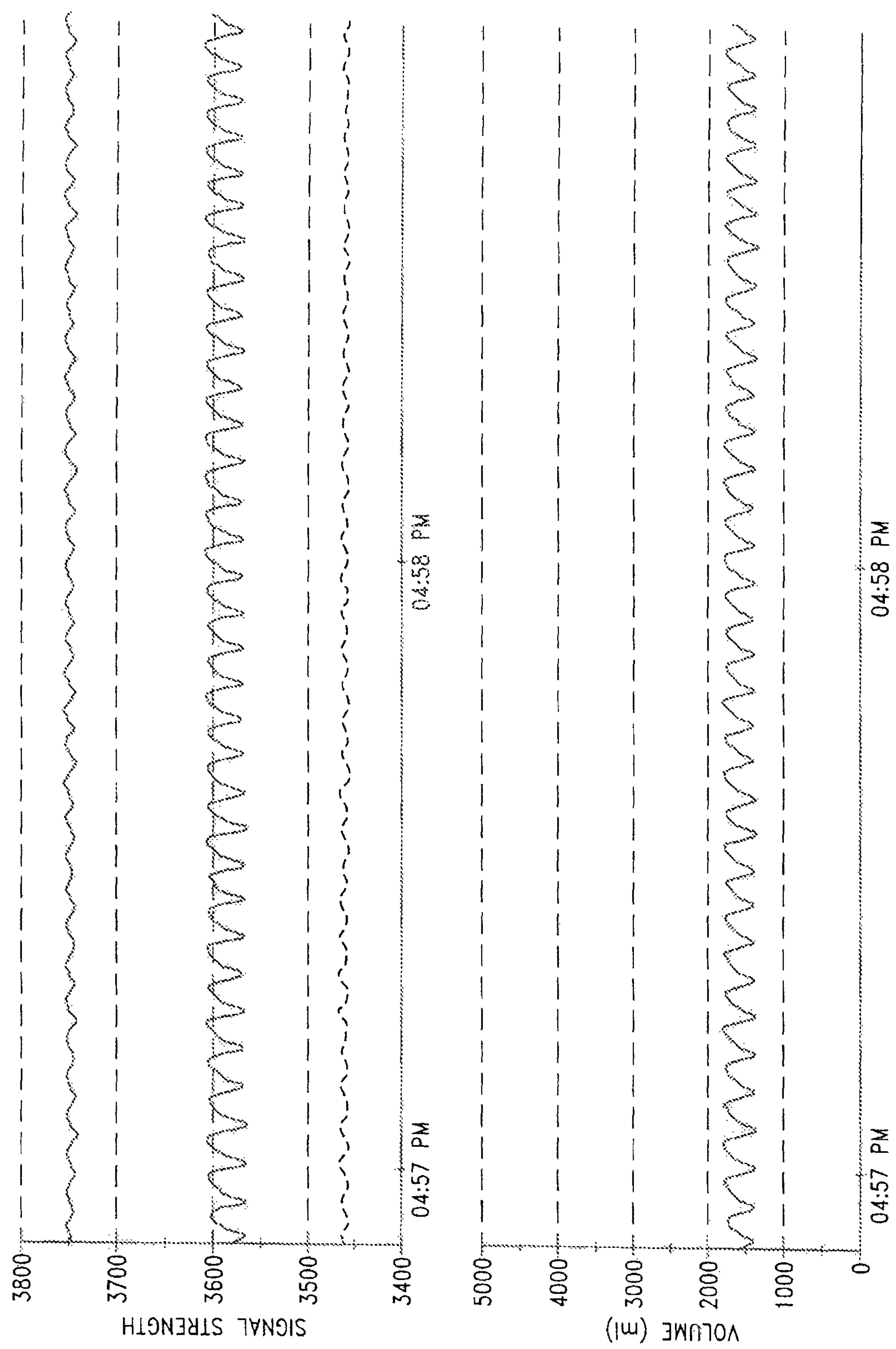
FIGS. 13-16 are exemplar recordings of magnetometer signals and associated derived tidal volumes for a subject.
Figure 14:
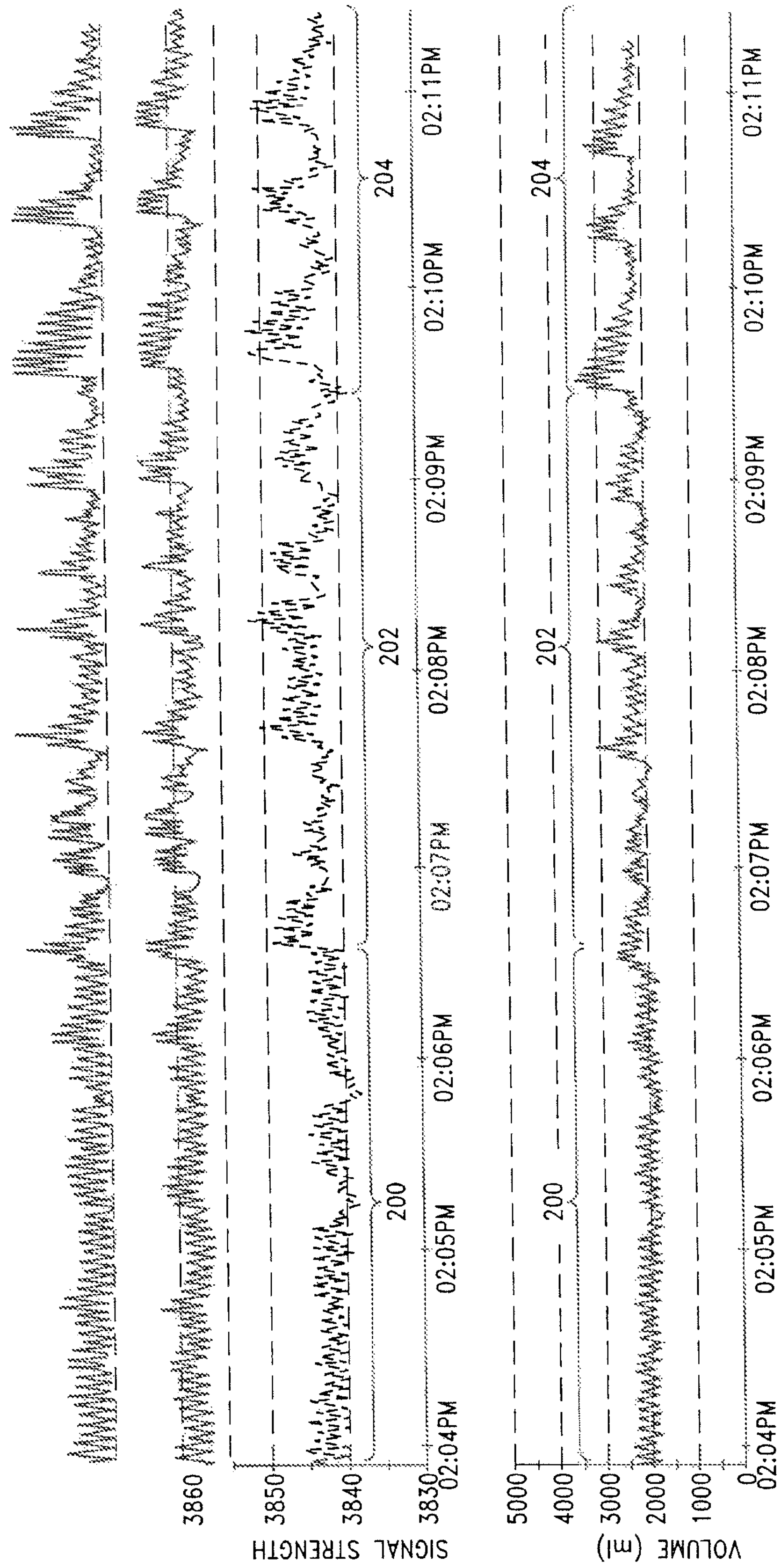
Figure 15:
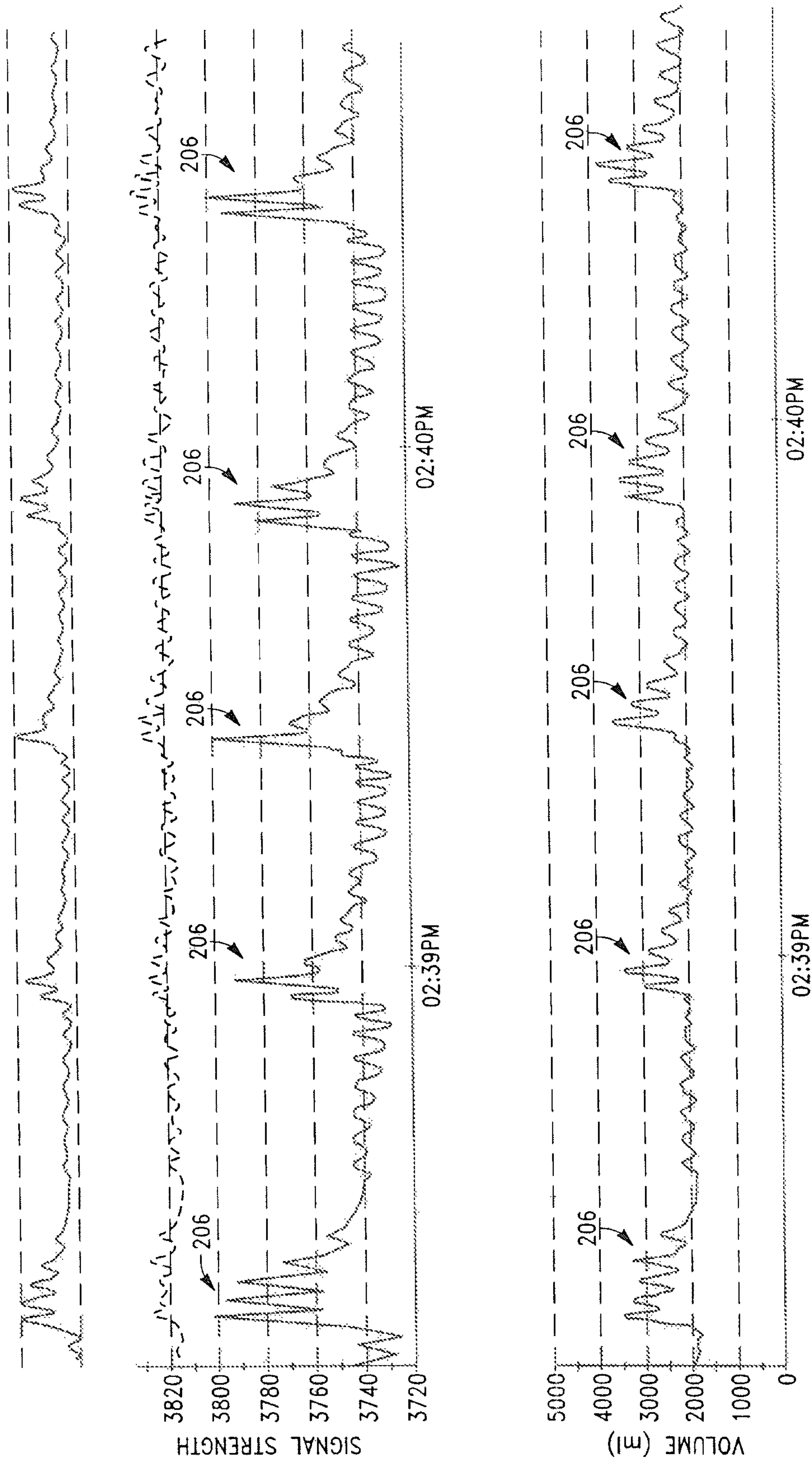
Figure 16:
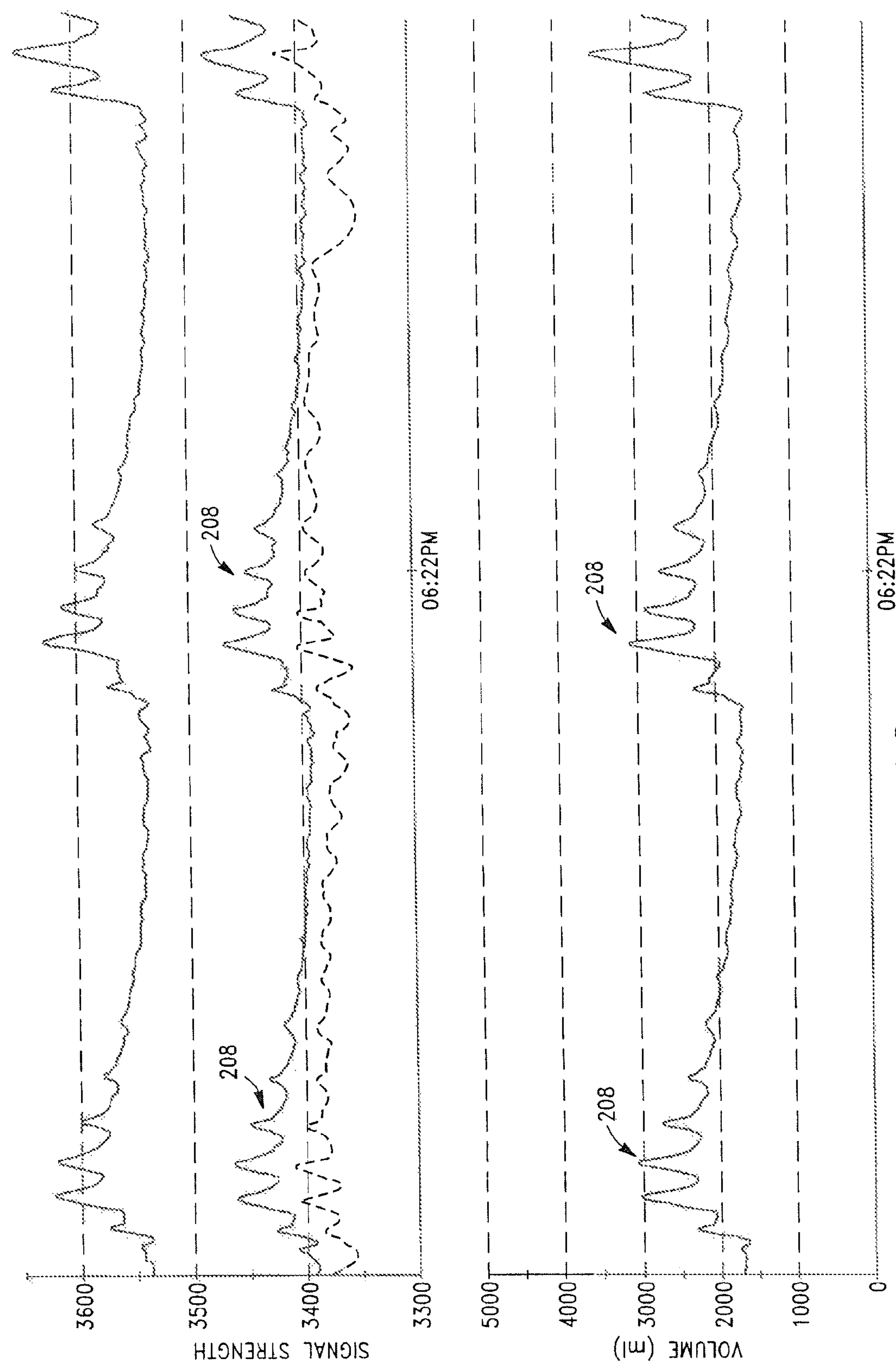

Exemplar recordings of magnetometer signals and associated derived tidal volume are shown in FIGS. 13-16; FIG. 13 reflecting quiet breathing of a subject during sleep with no apneas or hypopneas, FIG. 14 reflecting sleep onset of a subject (denoted generally "200") followed by hypopneas (denoted generally "202") and apneas (denoted generally "204"), FIG. 15 reflecting recurrent hypopneas (denoted generally "206"), and FIG. 16 reflecting recurrent apneas (denoted generally "208").

Scoring of the magnetometer data was conducted in 30 second intervals. No oxygen saturation or EEG arousals were employed in the scoring process.

Scoring comprised polysomnography (PSG) scores and the magnetometer system signals (or scores). Apnea and hypopnea indices (AHI), apnea indices (AI) and hypopnea indices (HI) were also recorded.

A respiratory event (i.e. apnea or hypopnea) or occurrence was defined as ≥50% reduction in $V_T$ with a trend that was sustained for ≥10 seconds. Apneas were identified when the volume tracing was almost flat (minor oscillations were ignored). Hypopneas were identified when the volume could be measures (i.e. >120 cc).

Statistical Analysis

The mean apnea, hypopnea count and indices were compared using the standard t-test. Means±standard deviation (mean±SD) was also determined.

Results

No significant differences were noted between the PSG scores and the MTG scores for the apnea and hypopnea index (AHI), apnea index (AI) and hypopnea index (HI). As reflected in Table 7, the mean±SD AHI for the PSG and MTG data were 38.9±30.5 and 42.5±27.9, respectively.

TABLE 7

| | PSG | | MTG | |
|---|---|---|---|---|
| Subject | A + H (n) | AHI (n/hr) | A + H (n) | ANI (n/hr) |
| 1 | 131 | 22.6 | 161 | 27.5 |
| 2 | 315 | 48.0 | 36.3 | 55.3 |
| 3 | 15 | 2.3 | 10 | 1.5 |
| 4 | 138 | 51.1 | 178 | 65.9 |
| 5 | 189 | 30.9 | 222 | 36.4 |
| 6 | 102 | 21.0 | 135 | 27.8 |
| 7 | 48 | 15.0 | 59 | 18.4 |
| 8 | 149 | 28.7 | 215 | 41.3 |
| 9 | 352 | 73.3 | 397 | 82.7 |
| 10 | 384 | 75.3 | 418 | 81.9 |
| 11 | 395 | 92.4 | 321 | 75.1 |
| 12 | 5 | 1.1 | 13 | 2.8 |
| 13 | 25 | 5.4 | 82 | 17.7 |
| 14 | 144 | 31.4 | 143 | 31.2 |
| 15 | 132 | 85.6 | 112 | 72.6 |
| Mean ± SD | 168.3 ± 133.0 | 38.9 ± 30.5 | 188.6 ± 133.2 | 42.5 ± 27.9 |

A + H: apnea and hypopnea count

Figure 17:
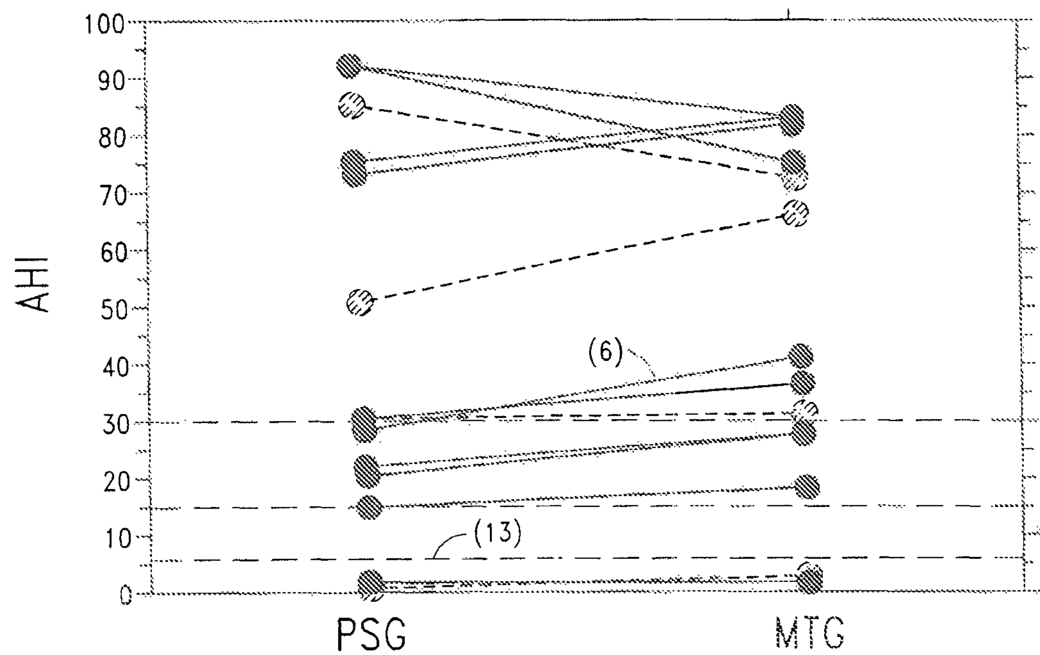
FIG. 17 is a graphical illustration of apnea and hypopnea indices for a plurality of monitored subjects, according to the invention.

Referring now to FIG. 17, there is shown a graphical illustration of the apnea and hypopnea indices (AHI) for all fifteen subjects. The dashed lines in FIG. 9 represent the limits of severity of sleep apnea, i.e. AHI 5-15 deemed mild sleep apnea, >15-30 deemed moderate sleep apnea, and >30 deemed severe sleep apnea.

As illustrated in FIG. 17, there was significant agreement in severity between PSG and MTG scores.

As reflected in Table 8, the mean±SD AI for the PSG and MTG data were 13.6±13.3 and 13.8±10.0, respectively.

TABLE 8

| | PSG | | MTG | |
|---|---|---|---|---|
| Subject | Apnea (n) | AI (n/hr) | Apnea (n) | AI (n/hr) |
| 1 | 30 | 5.2 | 48 | 8.2 |
| 2 | 98 | 14.9 | 121 | 18.4 |
| 3 | 3 | 0.5 | 3 | 0.5 |
| 4 | 54 | 20.0 | 70 | 25.9 |
| 5 | 63 | 10.3 | 86 | 14.1 |
| 6 | 14 | 2.9 | 35 | 7.2 |
| 7 | 12 | 3.7 | 10 | 3.1 |
| 8 | 61 | 11.8 | 87 | 16.7 |
| 9 | 50 | 10.4 | 92 | 19.2 |
| 10 | 108 | 21.2 | 153 | 30.0 |
| 11 | 143 | 33.5 | 135 | 31.6 |
| 12 | 0 | 0 | 0 | 0 |
| 13 | 10 | 2.2 | 42 | 9.1 |
| 14 | 91 | 19.9 | 38 | 8.3 |
| 15 | 73 | 47.4 | 22 | 14.3 |
| Mean ± SD | 54 ± 43.1 | 13.6 ± 13.3 | 62.8 ± 48.4 | 13.8 ± 10.0 |

Figure 18:
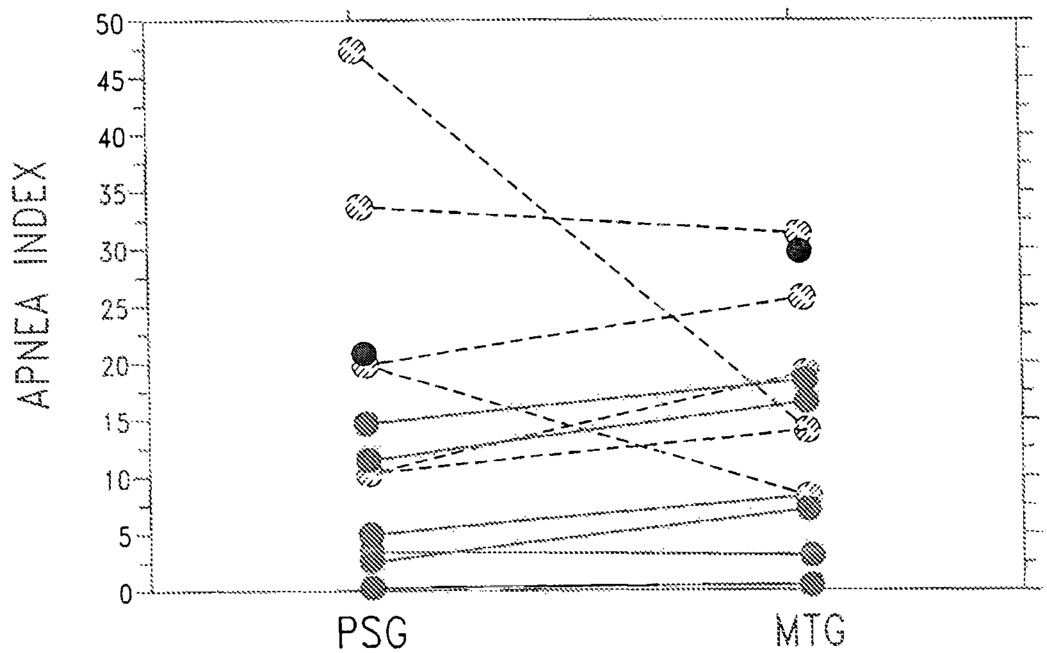
FIG. 18 is a graphical illustration of apnea indices for a plurality of monitored subjects, according to the invention.

As illustrated in FIG. 18, there was no statistically significant difference in the mean apnea index (AI) between the MTG and PSG scores.

Referring now to Table 9, the mean±SD HI for the PSG and MTG data were 25.6±20.3 and 28.8±19.5, respectively.

TABLE 9

| Subject | PSG Hypopnea (n) | PSG HI (n/hr) | MTG Hypopnea (n) | MTG HI (n/hr) |
|---|---|---|---|---|
| 1 | 101 | 17.4 | 113 | 19.3 |
| 2 | 217 | 33.1 | 242 | 36.9 |
| 3 | 12 | 1.8 | 7 | 1.0 |
| 4 | 84 | 31.1 | 108 | 40.0 |
| 5 | 126 | 20.6 | 136 | 22.3 |
| 6 | 88 | 18.1 | 100 | 20.6 |
| 7 | 36 | 11.3 | 49 | 15.3 |
| 8 | 88 | 16.9 | 128 | 24.6 |
| 9 | 302 | 62.9 | 305 | 63.5 |
| 10 | 276 | 54.1 | 265 | 51.9 |
| 11 | 252 | 58.9 | 186 | 43.5 |
| 12 | 5 | 1.1 | 13 | 2.8 |
| 13 | 15 | 3.2 | 40 | 8.6 |
| 14 | 53 | 14.6 | 105 | 22.9 |
| 15 | 59 | 38.3 | 90 | 58.4 |
| Mean ± SD | 114.3 ± 99.5 | 25.6 ± 20.3 | 125.8 ± 89.3 | 28.8 ± 19.5 |

Figure 19:
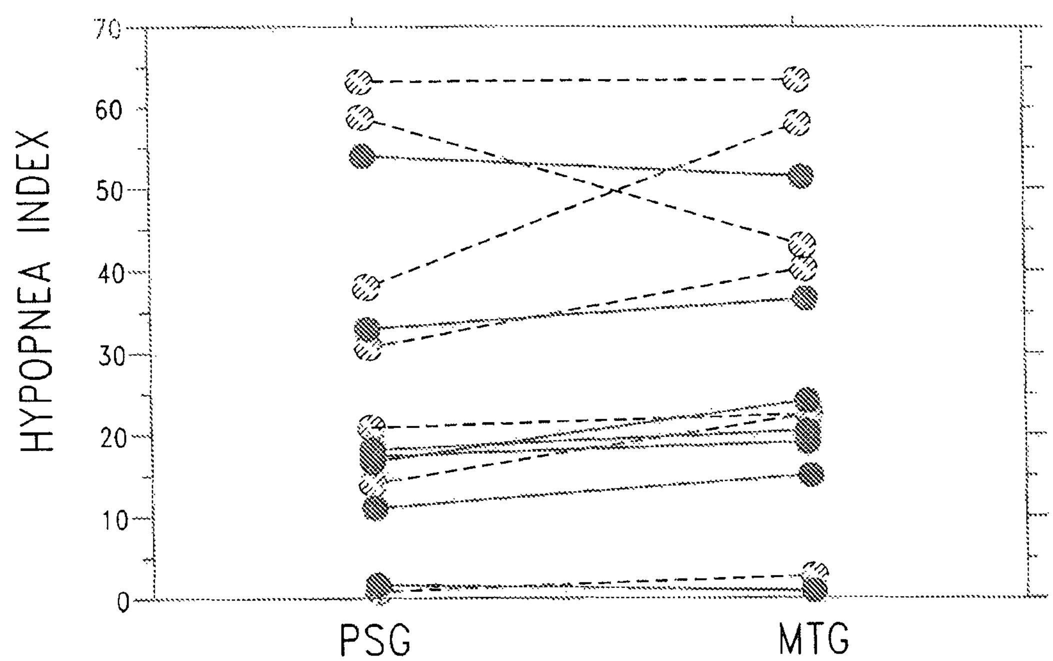
FIG. 19 is a graphical illustration of hypopnea indices for a plurality of monitored subjects, according to the invention.

As illustrated in FIG. 19, there was similarly no statistically significant difference in the mean hypopnea index (HI) between the MTG and PSG scores.

There was also significant agreement in the severity of sleep apnea (i.e. AHI 5-15 deemed mild, >15-30 deemed moderate, and >30 deemed severe) between the MTG and PSG scores. As reflected in FIG. 13, only two subjects had a change in the AHI from mild (i.e. 5.4/hr.) to moderate (i.e. 17.7/hr.), i.e. subject #13 (shown in parentheses) and from moderate (i.e. 28.7/hr.) to severe (41.3/hr.), i.e. subject #6, respectively.

This study thus demonstrates that the "three-degrees-of-freedom" model of the invention and a magnetometer system employing the subject model can accurately and readily detect apneas and hypopneas during sleep. The system can also readily establish the severity of sleep apnea.

As will be appreciated by one having ordinary skill in the art, the "three-degrees-of-freedom" models of the invention and ventilation (or magnetometer) systems employing the models can be readily employed to accurately determine ventilation parameters or characteristics, including total pulmonary ventilation, breathing frequency, inspiratory breathing time, expiratory breathing time and total breathing time. The noted ventilation parameters can be employed to identify normal breathing patterns at rest (while awake and during sleep) and during activities, with changes in posture, with exposure to pollutants, or to identify abnormal breathing patterns or respiratory events, such as those presented with respiratory dyskinesia, impending respiratory failure, exacerbations of emphysema, asthma and other forms of lung disease.

The ventilation parameters can also be readily employed to detect and characterize obstructive and central apneic episodes in adults and infants during sleep, calculate flow volume loops during exercise and sleep, characterize breathing patterns in individuals with undiagnosed causes of dyspnea, and determine the effects of air toxins on pulmonary and cardiovascular health.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A system for monitoring respiration of a subject, comprising: a first sensor system configured for substantially continuously determining a first anatomical characteristic representing a first linear displacement of the subject's rib cage in a first orientation; a second sensor system configured for substantially continuously determining a second anatomical characteristic representing a first linear displacement of the subject's abdomen in said first orientation, and for substantially continuously determining a third anatomical characteristic representing a first axial displacement of the subject's chest wall; a posture sensor configured for detecting when the subject is in one of a plurality of orientations; a memory configured to store a first empirical relationship that determines a rib cage volume-motion coefficient, an abdomen volume-motion coefficient, and a chest wall volume-motion coefficient, and a second empirical relationship that determines a ventilation characteristic as a function of said first, second and third anatomical characteristics and said rib cage, abdomen and chest wall volume-motion coefficients; and a processor configured for determining said ventilation parameter with said second empirical relationship and for determining a first ventilation parameter associated with said detected subject orientation, wherein one of the first and second sensor systems acquires a base-line ventilation characteristic, and a third empirical relationship correlates said acquired base-line ventilation characteristic to a ventilation parameter determined with said second empirical relationship.

2. The system of claim 1, wherein said third empirical relationship is stored in said memory.

3. The system of claim 1, wherein said first empirical relationship determines a plurality of said rib cage, abdomen and chest wall volume-motion coefficients, said plurality of rib cage, abdomen and chest wall volume-motion coefficients representing a plurality of body orientations and motions.

4. The system of claim 3, wherein said memory includes a plurality of volume-motion coefficient data sets, said plurality of volume-motion data sets including a first plurality of volume-motion coefficient data sets representing said plurality of orientations and a second plurality of volume-motion coefficient data sets representing said plurality of motions, each of said first plurality of volume-motion coefficient data sets comprising a respective one of said rib cage, abdomen and chest wall volume-motion coefficients that represent a respective one of said plurality of orientations, each of said second plurality of volume-motion coefficient data sets comprising a respective one of said rib cage, abdomen and chest wall volume-motion coefficients that represent a respective one of said plurality of motions.

5. The system of claim 4, wherein the posture sensor detects when the subject is exhibiting one of said motions.

6. The system of claim 5, wherein said third empirical relationship applies a selective one of said first and second plurality of volume-motion coefficient data sets representing one of said plurality of orientations or motions that corresponds to a detected subject orientation or motion to said first empirical relationship, whereby said processor determines a first ventilation parameter associated with said detected subject orientation or motion.

7. A system for monitoring respiration of a subject, comprising: a first sensor system configured to substantially continuously determine a first linear displacement of the subject's rib cage, said first sensor system including a first receive device and a first transmission device adapted to transmit at least a first signal; a second sensor system configured to substantially continuously determine a first linear displacement of the subject's abdomen, said second sensor system including a second transmission device adapted to transmit at least a second signal and a second receive device adapted to receive said second signal, said first receive device being adapted to continuously receive said first and second signals, said second signal representing a first axial displacement of the subject's chest wall; a memory configured to store: a first empirical relationship that determines a rib cage volume-motion coefficient, an abdomen volume-motion coefficient, and a chest wall volume-motion coefficient and a second empirical relationship determines a ventilation characteristic as a function of said first linear displacement of the subject's rib cage, said first linear displacement of the subject's abdomen, said first axial displacement of the subject's chest wall, and said rib cage, abdomen and chest wall volume-motion coefficients, and an element analysis program configured to reduce noise in one of the first or second signals; and a processor configured for determining said ventilation parameter with said second empirical relationship, wherein each of said first and second receive devices is adapted to receive said first and second signals.

8. The system of claim 7, wherein said first and second receive devices and said first and second transmission devices comprise magnetometer coils.

9. The system of claim 7, wherein said first and second receive devices and said first and second transmission devices comprise Hall effect sensors.

* * * * *